US008623865B2

(12) United States Patent
Gerusz et al.

(10) Patent No.: US 8,623,865 B2
(45) Date of Patent: Jan. 7, 2014

(54) ACYLPIPERAZINONES AND THEIR USE AS PHARMACEUTICALS

(71) Applicant: Fab Parma S.A.S, Paris (FR)

(72) Inventors: Vincent Gerusz, Paris (FR); Sonia Escaich, Paris (FR); Mayalen Oxoby, Paris (FR); Francois Moreau, Paris (FR)

(73) Assignee: Fab Pharma S.A.S., Paris (FR)

( * ) Notice: Subject to any disclaimer, the term of this patent is extended or adjusted under 35 U.S.C. 154(b) by 0 days.

(21) Appl. No.: 13/741,447

(22) Filed: Jan. 15, 2013

(65) Prior Publication Data

US 2013/0137689 A1    May 30, 2013

Related U.S. Application Data

(63) Continuation of application No. 13/503,223, filed as application No. PCT/EP2010/065811 on Oct. 20, 2010, now Pat. No. 8,383,621.

(60) Provisional application No. 61/253,354, filed on Oct. 20, 2009.

(51) Int. Cl.
*A61K 31/5377* (2006.01)
*A61K 31/496* (2006.01)

(52) U.S. Cl.
USPC .................................. 514/235.8; 514/255.01

(58) Field of Classification Search
None
See application file for complete search history.

(56) References Cited

U.S. PATENT DOCUMENTS

2010/0041658 A1*  2/2010  Denis et al. ................ 514/238.2
2012/0232079 A1   9/2012  Gerusz et al.

FOREIGN PATENT DOCUMENTS

WO    WO 2007/135562    11/2007

OTHER PUBLICATIONS

International Search Report for PCT/EP2010/065811 mailed Jan. 19, 2011.
Written Opinion of the International Searching Authority mailed Jan. 19, 2011.
S. Tipparaju et al., "Design and Synthesis of Aryl Ether Inhibitors of the Bacillus Anthracis Anoyl-ACP Reductase", Chemmedchem, Aug. 2008, vol. 3, No. 8, pp. 1250-1268.

* cited by examiner

*Primary Examiner* — Kamal Saeed
(74) *Attorney, Agent, or Firm* — Nixon & Vanderhye P.C.

(57) ABSTRACT

The invention relates to novel acylpiperazinone compounds, to the preparation of the compounds and intermediates used therein, to the use of the compounds as antibacterial medicaments and pharmaceutical compositions containing the compounds.

20 Claims, 2 Drawing Sheets

ACYLPIPERAZINONES AND THEIR USE AS PHARMACEUTICALS

This application is a continuation of application Ser. No. 13/503,223 (now U.S. Pat. No. 8,383,621, issued Feb. 26, 2013), filed Jun. 1, 2012 (published as US 2012-0232079-A1), which is a U.S. national phase of PCT/EP2010/065811, filed Oct. 20, 2010, which designated the U.S. and claims benefit of U.S. Provisional Application No. 61/253,354, filed Oct. 20, 2009, the entire contents of each of which are hereby incorporated herein by reference.

FIELD OF THE INVENTION

The invention relates to novel acylpiperazinone compounds, to the preparation of the compounds and intermediates used therein, to the use of the compounds as antibacterial medicaments and pharmaceutical compositions containing the compounds.

BACKGROUND OF THE INVENTION

The invention particularly relates to new compounds capable of inhibiting bacterial and/or parasite fatty acid biosynthesis and their use as antibacterial and/or antiparasitic agents.

The emergence of antibiotic-resistant pathogens has become a serious worldwide healthcare problem. Indeed, some infections are now caused by multi-drug resistant organisms that are no longer responsive to currently available treatments. There is therefore an immediate need for new antibacterial/antiparasitic agents with a novel mode of action.

The bacterial fatty acid biosynthesis (FASII system) has recently generated a lot of interest for the development of novel antibacterial/antiparasitic agents (Rock et al. *J. Biol. Chem.* 2006, 281, 17541; Wright and Reynolds *Curr. Opin. Microbiol.* 2007, 10, 447). The organization of components in the bacterial fatty acid biosynthesis pathway based on discrete enzymes is fundamentally different from the multifunctional FASI system found in mammals, therefore allowing good prospects of selective inhibition. The overall high degree of conservation in many enzymes of the bacterial FASII system should also allow the development of broader-spectrum antibacterial/antiparasitic agents.

Among all the monofunctional enzymes of the bacterial FASII system, FabI represents the enoyl-ACP reductase responsible of the last step of the fatty acid biosynthetic elongation cycle. Using the cofactor NAD(P)H as a hydride source, FabI reduces the double bond in the trans-2-enoyl-ACP intermediate to the corresponding acyl-ACP product. This enzyme has been shown to constitute an essential target in major pathogens such as *E. coli* (Heath et al. *J. Biol. Chem.* 1995, 270, 26538; Bergler et al. *Eur. J. Biochem.* 1996, 242, 689) and *S. aureus* (Heath et al. *J. Biol. Chem.* 2000, 275, 4654). However, other isoforms have been isolated such as FabK from *S. pneumoniae* (Heath et al. *Nature* 2000, 406, 145) and FabL from *B. subtilis* (Heath et al. *J. Biol. Chem.* 2000, 275, 40128). Although FabK is structurally and mechanistically unrelated to FabI (Marrakchi et al. *Biochem J.* 2003, 370, 1055), the similarity of FabI with FabL (*B. subtilis*), InhA (*M. tuberculosis*) and PfENR (*P. falciparum*) still offers opportunities of interesting activity spectra (Heath et al. *Prog. Lipid Res.* 2001, 40, 467).

Several FabI inhibitors have already been reported in the literature (Tonge et al. *Acc. Chem. Res.* 2008, 41, 11). Some of them such as diazaborines (Baldock et al. *Science* 1996, 274, 2107) and isoniazid in its activated form (Tonge et al. *Proc. Natl. Acad. Sci. U.S.A.* 2003, 100, 13881) act by covalently modifying the cofactor NAD+. However some drawbacks are associated with these products. Diazaborines are only used experimentally because of their inherent toxicity (Baldock et al. *Biochem. Pharmacol.* 1998, 55, 1541) while isoniazid is a prodrug restricted to the treatment of susceptible tuberculosis. The fact that isoniazid requires activation by hydrogen-peroxyde inducible enzymes (Schultz et al. *J. Am. Chem. Soc.* 1995, 117, 5009) enhances the possibilities of resistance by lack of activation or increased detoxification (Rosner et al. *Antimicrob. Agents Chemother.* 1993, 37, 2251 and ibid 1994, 38, 1829).

Other inhibitors act by interacting noncovalently with the enzyme-cofactor complex. For instance Triclosan, a widely used consumer goods preservative with broad spectrum anti-microbial activity, has been found to be a reversible, tight-binding inhibitor of *E. coli* FabI (Ward et al. *Biochemistry* 1999, 38, 12514). Intravenous toxicology studies on this compound indicated a $LD_{50}$ on rats of 29 mg/kg clearly ruling out intravenous injection (Lyman et al. *Ind. Med. Surg.* 1969, 38, 42). Derivatives based on the 2-hydroxydiphenyl ether core of Triclosan have been reported (Tonge et al. *J. Med. Chem.* 2004, 47, 509, *ACS Chem. Biol.* 2006, 1, 43 and *Bioorg. Med. Chem. Lett.* 2008, 18, 3029; Surolia et al. *Bioorg. Med. Chem.* 2006, 14, 8086 and ibid 2008, 16, 5536; Freundlich et al. *J. Biol. Chem.* 2007, 282, 25436) as well as other inhibitors based on various classes of high throughput screening derived templates (Seefeld et al. *Bioorg. Med. Chem. Lett.* 2001, 11, 2241 and *J. Med. Chem.* 2003, 46, 1627; Heerding et al. *Bioorg. Med. Chem. Lett.* 2001, 11, 2061; Miller et al. J. Med. Chem. 2002, 45, 3246; Payne et al. *Antimicrob. Agents Chemother.* 2002, 46, 3118; Sacchettini et al. *J. Biol. Chem.* 2003, 278, 20851; Moir et al. *Antimicrob. Agents Chemother.* 2004, 48, 1541; Montellano et al. *J. Med. Chem.* 2006, 49, 6308; Kwak et al. *Int. J. Antimicro. Ag.* 2007, 30, 446; Lee et al. *Antimicrob. Agents Chemother.* 2007, 51, 2591; Kitagawa et al. *J. Med. Chem.* 2007, 50, 4710, *Bioorg. Med. Chem.* 2007, 15, 1106 and *Bioorg. Med. Chem. Lett.* 2007, 17, 4982; Takahata et al. *J. Antibiot.* 2007, 60, 123; Kozikowski et al. *Bioorg. Med. Chem. Lett.* 2008, 18, 3565), nevertheless none of these inhibitors have succeeded yet as a drug. Interestingly, some classes of these inhibitors display activity on both FabI and FabK: predominantly FabK for the dual compounds based on phenylimidazole derivatives of 4-pyridones (Kitagawa et al. *J. Med. Chem.* 2007, 50, 4710), predominantly FabI for the indole derivatives (Payne et al. *Antimicrob. Agents Chemother.* 2002, 46, 3118; Seefeld et al. *J. Med. Chem.* 2003, 46, 1627). However, the moderate activity on the second enzyme might prove to be a drawback for such compounds as it may lead to an increase of resistance mechanisms due to the added selection pressure (Tonge et al. *Acc. Chem. Res.* 2008, 41, 11).

Despite the attractiveness of FabI as an antibacterial/anti-parasitic target, it is still largely unexploited at this time since there are no drugs on the market or within advanced clinical phases.

WO 2007/135562 (Mutabilis SA) describes a series of hydroxyphenyl derivatives that display a selective spectrum of activity on species containing FabI and related targets, in contrast to Triclosan.

One of the purposes of the invention is to provide novel compounds active on FabI and related targets with improved pharmacological properties over existing compounds.

SUMMARY OF THE INVENTION

According to a first aspect of the invention, there is provided a compound of formula (I):

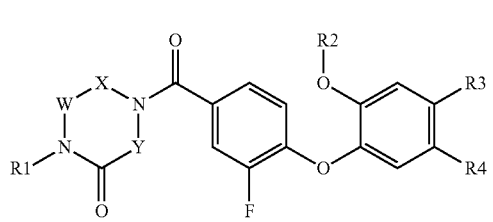

(I)

wherein:
W, X and Y independently represent $CH_2$ or C=O, wherein said $CH_2$ group may be optionally independently substituted by a fluorine or $(C_1-C_6)$ alkyl group, wherein said $(C_1-C_6)$ alkyl group may be further substituted by one or two R5 groups;

R1 represents H, $(C_1-C_6)$ alkyl optionally substituted by a $CONR_aR_b$ group, $(C_2-C_6)$ alkenyl, $(C_2-C_6)$ alkynyl, phenyl or a —Z-Het group, such that Z represents a bond or a linker selected from CO, $(C_1-C_6)$ alkylene or —CO—$(C_1-C_6)$ alkylene and Het represents a 4-6 membered monocyclic saturated or unsaturated heterocycle containing 1-3 heteroatoms selected from N, O and S, wherein said phenyl or heterocycle group of R1 may be optionally substituted by one or more (e.g. 1, 2 or 3) R5 groups;

R2 represents H, $CO_2R_a$, $COR_a$, $CONR_aR_b$, $CH_2OR_c$, $CH_2NR_aR_b$, $SO_2NR_aR_b$ or $P(O)OR_aOR_b$;

R3 represents halogen, $(C_1-C_6)$ alkyl, $(C_2-C_6)$ alkenyl or $(C_2-C_6)$ alkynyl;

R4 represents H, halogen, CN or $CH_3$;

$R_a$, $R_b$ and $R_c$ independently represent H, $(C_1-C_6)$ alkyl, $(C_2-C_6)$ alkenyl, $(C_2-C_6)$ alkynyl, or an $NR_aR_b$ group may optionally form a 3- to 7-membered nitrogen containing saturated heterocycle optionally containing 1 to 3 additional heteroatoms selected from N, O or S wherein said heterocycle may be optionally substituted by one or more $(C_1-C_6)$ alkyl groups;

R5 represents halogen, CN, $(C_1-C_6)$ alkyl, $(C_2-C_6)$ alkenyl, $(C_2-C_6)$ alkynyl, $CO_2R_a$, $COR_a$, $CONR_aR_b$, $OCOR_a$, $OR_aNR_aR_b$, ON=$CR_aR_b$, $NR_cCOR_a$, $NR_cCOOR_a$, $OCONR_aR_b$, $NR_cCONR_aR_b$, $NR_cSO_2R_a$, $S(O)_nR_a$, or $SO_2NR_aR_b$;

n represents an integer selected from 0 to 2;
or a pharmaceutically acceptable salt or solvate thereof.

DETAILED DESCRIPTION OF THE INVENTION

Figure 1:
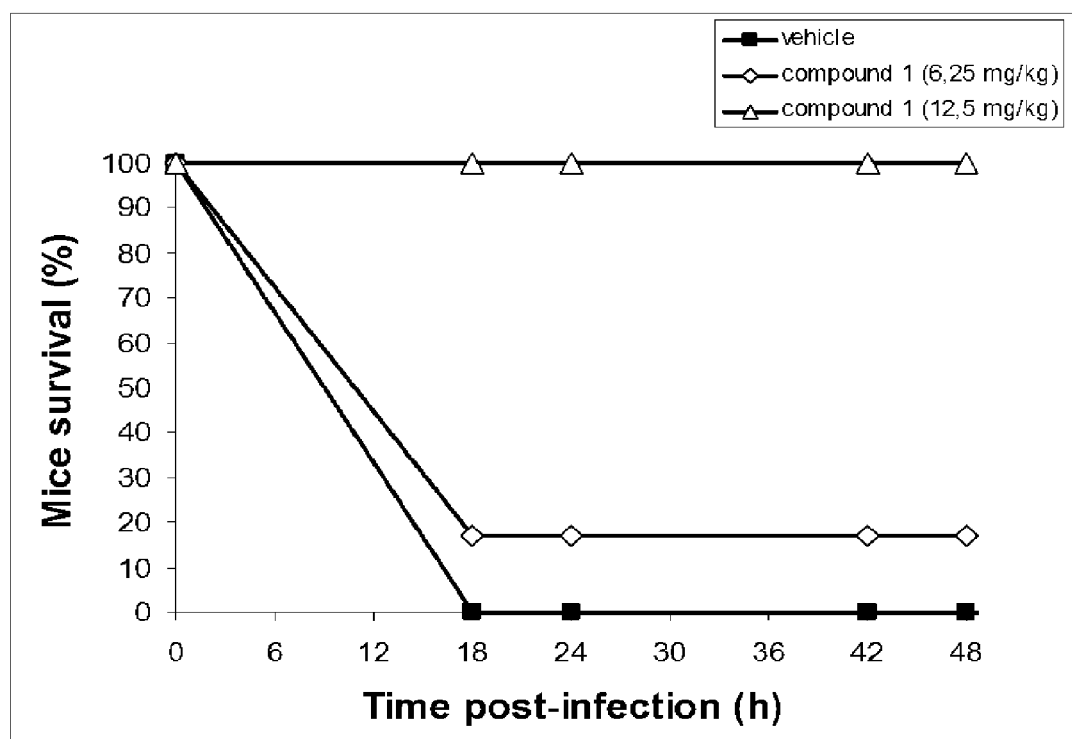
FIG. 1 relates to survival of infected mice after a single subcutaneous treatment of the compound of Example 1.

The compounds of the invention have good in vitro and/or in vivo activity and display surprisingly less serum binding than previously described hydroxyphenyl derivatives as confirmed by data presented herein. Especially, the compounds of the invention have the ability to interact less with serum and also the ability to be active via oral administration.

In the present context, the term "pharmaceutically acceptable salt" is intended to indicate salts which are not harmful to the patient. Such salts include pharmaceutically acceptable acid addition salts, pharmaceutically acceptable metal salts and pharmaceutically acceptable akaline addition salts. Acid addition salts include salts of inorganic acids as well as organic acids.

Representative examples of suitable inorganic acids include hydrochloric, hydrobromic, hydroiodic, phosphoric, sulfuric, nitric acids and the like.

Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Representative examples of alkaline salts include, for example, sodium, potassium, lithium, calcium, magnesium or ammonium or organic bases such as, for example, methylamine, ethylamine, propylamine, trimethylamine, diethylamine, triethylamine, N,N-dimethylethanolamine, tris(hydroxymethyl)aminomethane, ethanolamine, pyridine, piperidine, piperazine, picoline, dicyclohexylamine, morpholine, benzylamine, procaine, lysine, arginine, histidine, N-methylglucamine.

According to the invention, the compounds of formula (I) can be in racemic forms, as well as in the form of pure enantiomers or non racemic (scalemic) mixture of enantiomers, including when the compounds of formula (I) have more than one stereogenic centre. In case the compounds of formula (I) have unsaturated carbon carbon double bonds, both the cis (Z) and trans (E) isomers and their mixtures belong to the invention.

References herein to "halogen" means a fluorine, chlorine, bromine or iodine atom.

References herein to "$(C_1-C_6)$ alkyl" means any linear, branched hydrocarbon groups having 1 to 6 carbon atoms, or cyclic hydrocarbon groups having 3 to 6 carbon atoms. Representative examples of such alkyl groups include methyl, ethyl, n-propyl, isopropyl, n-butyl, isobutyl and t-butyl, n-pentyl, isopentyl, neopentyl, cyclopropyl, cyclobutyl, cyclopentyl and cyclohexyl. References to "halo$(C_1-C_6)$ alkyl" mean a $(C_1-C_6)$ alkyl group substituted by one or more halogen atoms as herein defined.

References herein to "$(C_2-C_6)$ alkenyl" means any linear, branched hydrocarbon groups of 2 to 6 carbon atoms, or cyclic hydrocarbon group having 3 to 6 carbon atoms having at least one double bond. Representative examples of such alkenyl groups include ethenyl, propenyl, butenyl and cyclohexenyl. References to "halo$(C_2-C_6)$ alkenyl" mean a $(C_2-C_6)$ alkenyl group substituted by one or more halogen atoms as herein defined.

References herein to "$(C_2-C_6)$ alkynyl" means any linear, or branched hydrocarbon groups of 2 to 6 carbon atoms, having at least one triple bond. Representative examples of such alkynyl groups include ethynyl, propargyl and butynyl. References to "halo($C_2$-$C_6$) alkynyl" mean a ($C_2$-$C_6$) alkynyl group substituted by one or more halogen atoms as herein defined.

Illustrative examples of "Het" within the definition of R1 include those selected from the group comprising furyl, tetrahydrofuryl, thienyl, tetrahydrothienyl, pyrrolyl, pyrrolidinyl, oxazolyl, oxazolinyl, oxazolidinyl, isoxazolyl, thiazolyl, thiazolinyl, thiazolidinyl, isothiazolyl, imidazolyl, pyrazolyl, indazolyl, tetra-hydroindazolyl, triazolyl, oxadiazolyl, thiadiazolyl, tetrazolyl, pyranyl, tetrahydropyranyl, dioxanyl, dioxolanyl, pyridinyl, pyridonyl, piperidinyl, tetrahydropyridinyl, quinolinyl, isoquinolinyl, tetra- and perhydro-quinolinyl and isoquinolinyl, pyrimidinyl, quinazolinyl, pyrazinyl, pyrazidinyl, piperazinyl, quinoxalinyl, piridazinyl, triazinyl, oxetanyl, azetidinyl and morpholinyl.

Illustrative examples of saturated nitrogen containing heterocycles within the definition of NRaRb include those selected from the group comprising, pyrrolidinyl, oxazolidinyl, thiazolidinyl, piperidinyl, piperazinyl and morpholinyl.

In one embodiment, W, X and Y represents $CH_2$ optionally independently substituted by a ($C_1$-$C_6$) alkyl group, wherein said ($C_1$-$C_6$) alkyl group may be further substituted by one or two R5 groups.

When W, X or Y represent $CH_2$ substituted by a ($C_1$-$C_6$) alkyl group wherein said ($C_1$-$C_6$) alkyl group is optionally substituted by one or two R5 groups, representative examples of such W, X or Y groups include —CH—$CH_3$, —CH—$CH_2$—OH, —CH—$CH_2$—$CONH_2$, —CH—$CH_2$—$CONMe_2$ and —CH—$CH_2$—CO-(4-methylpiperazin-1-yl). In one embodiment, W, X and Y each represent $CH_2$ optionally independently substituted by an unsubstituted ($C_1$-$C_6$) alkyl group. In a further embodiment, W and X both represent $CH_2$ and Y represents —CH—$CH_3$. In a further embodiment, W, X and Y each represent $CH_2$.

In an alternative embodiment, W represents C=O and X and Y both represent $CH_2$.

When R1 represents a —Z-Het group, representative examples of such a —Z-Het group include —CO—$CH_2$-morpholinyl, —$CH_2$-morpholinyl and —($CH_2$)$_2$-morpholinyl. In one embodiment, R1 represents —$CH_2$-morpholinyl.

When R1 represents ($C_1$-$C_6$) alkyl optionally substituted by a CONRaRb group, a representative example of such an R1 group is —$CH_2$—$CONH_2$.

In one embodiment, R1 represents H, ($C_1$-$C_6$) alkyl (i.e. methyl), ($C_1$-$C_6$) alkyl optionally substituted by a CONRaRb group (i.e. —$CH_2$—$CONH_2$) or a —Z-Het group (i.e. —$CH_2$-morpholinyl).

In a further embodiment, R1 represents H, ($C_1$-$C_6$) alkyl, ($C_2$-$C_6$) alkenyl, ($C_2$-$C_6$) alkynyl, phenyl or a 4-6 membered monocyclic saturated or unsaturated heterocycle containing 1-3 heteroatoms selected from N, O and S, wherein said phenyl or heterocycle group of R1 may be optionally substituted by one or more (e.g. 1, 2 or 3) R5 groups. In a further embodiment, R1 represents H, ($C_1$-$C_6$) alkyl, ($C_2$-$C_6$) alkenyl or ($C_2$-$C_6$) alkynyl. In a yet further embodiment, R1 represents H or ($C_1$-$C_6$) alkyl. In a yet further embodiment, R1 represents H or ($C_1$-$C_6$) alkyl (e.g. methyl). In a yet further embodiment, R1 represents H. In a still yet further embodiment, R1 represents a —Z-Het group, such as —CO—$CH_2$-morpholinyl, —$CH_2$-morpholinyl or —($CH_2$)$_2$-morpholinyl, in particular, R1 represents —$CH_2$-morpholinyl.

In one embodiment, R2 represents H, $CO_2R_a$, $COR_a$, $CONR_aR_b$, $CH_2OR_c$ or $CH_2NR_aR_b$. In a further embodiment, R2 represents H, $CO_2R_a$, $COR_a$ or $CONR_aR_b$. In a yet further embodiment, R2 represents H, $CO_2R_a$ or $COR_a$. In a yet further embodiment, R2 represents H or $CO_2R_a$. In a yet further embodiment, R2 represents H or —$CO_2$-ethyl. In a yet further embodiment, R2 represents H.

In one embodiment, R3 represents halogen or ($C_1$-$C_6$) alkyl. In a further embodiment, R3 represents halogen, such as Br or Cl, or ($C_1$-$C_6$) alkyl, such as methyl, ethyl or propyl. In a yet further embodiment, R3 represents ethyl.

In one embodiment, R4 represents H, halogen, such as F or Cl, or $CH_3$. In a further embodiment, R4 represents H or halogen, such as F or Cl. In a yet further embodiment, R4 represents H or F. In a yet further embodiment, R4 represents F. In an alternative embodiment, R4 represents H.

In one embodiment, $R_5$ independently represents halogen (e.g. F), ($C_1$-$C_6$) alkyl, ($C_2$-$C_6$) alkenyl, ($C_2$-$C_6$) alkynyl, $COR_a$, $CONR_aR_b$, $OR_a$, $NR_aR_b$, $NR_cCOR_a$, $S(O)_nR_a$, or $SO_2NR_aR_b$.

In one embodiment, $R_a$ and $R_b$ independently represent H, ($C_1$-$C_6$) alkyl, ($C_2$-$C_6$) alkenyl or ($C_2$-$C_6$) alkynyl. In a further embodiment, $R_a$ and $R_b$ independently represent H or ($C_1$-$C_6$) alkyl. In a yet further embodiment, $R_a$ and $R_b$ each represent ($C_1$-$C_6$) alkyl, such as methyl, ethyl or propyl. In a yet further embodiment, $R_a$ represents ethyl.

In an alternative embodiment, $NR_aR_b$ form a 3- to 7-membered nitrogen containing heterocycle optionally containing 1 to 3 additional heteroatoms selected from N, O or S, such as piperazinyl or morpholinyl, wherein said heterocycle is optionally substituted by one or more ($C_1$-$C_6$) alkyl groups. In a further embodiment, $NR_aR_b$ form a piperazine ring optionally substituted by one or more ($C_1$-$C_6$) alkyl groups (such as 4-methyl-piperazin-1-yl).

In one embodiment, $R_c$ represents H or ($C_1$-$C_6$) alkyl. In a further embodiment, $R_c$ represents H or methyl. In a yet further embodiment, $R_c$ represents H.

In one embodiment, n represents 1 or 2. In a further embodiment, n represents 2.

In one embodiment, the compound of formula (I) is selected from:
4-[4-(4-Ethyl-5-fluoro-2-hydroxyphenoxy)-3-fluorobenzoyl]piperazin-2-one (E1);
4-[4-(4-Ethyl-2-hydroxyphenoxy)-3-fluorobenzoyl]piperazin-2-one (E2); and
4-Fluoro-2-{2-fluoro-4-[(3-oxopiperazin-1-yl)carbonyl]phenoxy}-5-ethylphenyl ethyl carbonate (E3);
or a pharmaceutically acceptable salt or solvate thereof.

In a yet further embodiment, the compound of formula (I) is selected from:
4-[4-(4-Ethyl-5-fluoro-2-hydroxyphenoxy)-3-fluorobenzoyl]piperazine-2,6-dione (E4);
4-[4-(4-Ethyl-5-fluoro-2-hydroxyphenoxy)-3-fluorobenzoyl]-1-methylpiperazin-2-one (E5);
2-[4-(4-(4-Ethyl-5-fluoro-2-hydroxyphenoxy)-3-fluorobenzoyl]-2-oxopiperazin-1-yl)acetamide (E6);
4-[4-(4-Ethyl-5-fluoro-2-hydroxyphenoxy)-3-fluorobenzoyl]-1-(morpholinomethyl)piperazin-2-one (E7);
4-[4-(4-Ethyl-5-fluoro-2-hydroxyphenoxy)-3-fluorobenzoyl]-3-methyl piperazin-2-one (E8);
or a pharmaceutically acceptable salt or solvate thereof.

In a yet further embodiment, the compound of formula (I) is 4-[4-(4-Ethyl-5-fluoro-2-hydroxyphenoxy)-3-fluorobenzoyl]piperazin-2-one (E1) or a pharmaceutically acceptable salt or solvate thereof.

In a still yet further embodiment, the compound of formula (I) is 4-[4-(4-Ethyl-5-fluoro-2-hydroxyphenoxy)-3-fluorobenzoyl]-1-(morpholinomethyl)piperazin-2-one (E7).

The compounds of formula (I) and their salts may be prepared by processes known to the skilled chemist to be applicable for preparing chemically related compounds. Such processes use known starting materials or intermediates which may be obtained by standard procedures of organic chemistry. The following processes provide a variety of non-limiting routes for the production of the compounds of formula (I) and their intermediates used therein. These processes constitute further aspects of the invention.

According to a further aspect of the invention, there is provided a process for preparing a compound of formula (I) as defined above which comprises:

(a) reacting a carboxylic acid derivative of formula (II):

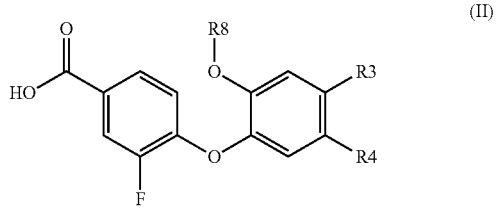

wherein R3 and R4 are as defined above for compounds of formula (I) and R8 represents a suitable protecting group, such as a ($C_{1-6}$) alkyl group, with a compound of formula (III):

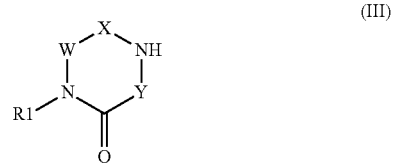

wherein W, X, Y and R1 are as defined above for compounds of formula (I), followed by:

(b) deprotecting a protected derivative of compound (I); and optionally thereafter followed by:

(c) interconversion of a compound of formula (I) to a further compound of formula (I).

Process (a) typically comprises the use of suitable coupling conditions known to one skilled in the art, a non-limiting example comprises the use of EDAC or (COCl)$_2$, a base such as TEA or DIPEA or DMAP, the optional use of HOBt, and a solvent such as DMF or DCM, to afford the protected derivatives of formula (I).

Process (b) typically comprises any suitable Lewis acid, for example BBr$_3$ or BCl$_3$, under conditions to yield the desired compounds of formula (I) wherein R2 represents a hydrogen atom.

Process (c) typically comprises interconversion procedures known by one skilled in the art. For example, compounds of formula (I) in which R2 represents hydrogen may be converted by methods known by one skilled in the art into compounds of formula (I) in which $R_2$ represents $CO_2R_a$, $COR_a$, $CONR_aR_b$, $CH_2OR_c$, $CH_2NR_aR_b$, $SO_2NR_aR_b$, $P(O)OR_aOR_b$, wherein $R_a$, $R_b$ and $R_c$ are as defined above for compounds of formula (I). Furthermore, compounds of formula (I) in which R1 represents hydrogen may be converted into compounds of formula (I) in which R1 represents —Z-Het (in particular wherein Z represents —CH$_2$—) by reacting a compound of formula (I) wherein R1 represents hydrogen with Het and formaldehyde in the presence of a suitable solvent such as methanol.

Compounds of formula (II) may be prepared in accordance with the following procedure:

(i) reacting a phenol derivative of formula (IV)

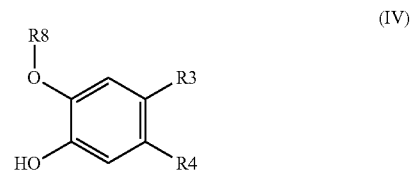

wherein R3, R4 and R8 are as defined above for compounds of formula (II), with a compound of formula (V):

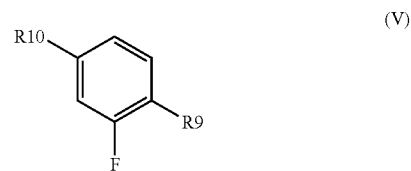

wherein R10 is either a nitrile, an ester or an amide substituent and R9 is a suitable leaving group such as a halogen atom or a nitro group capable of reacting with the OH group of compounds of formula (IV) under basic conditions known to one skilled in the art to afford a compound of formula (VI):

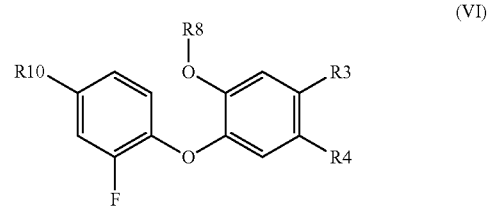

(ii) hydrolyzing the R10 moiety of a compound of formula (VI) in suitable aqueous acidic or basic conditions, for example 1N HCl or 6N NaOH, respectively, to yield the desired compound of formula (II):

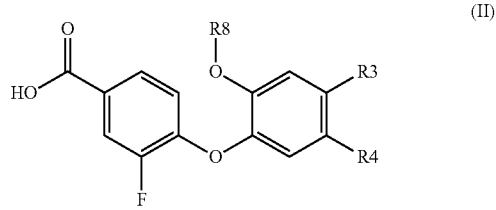

If appropriate, the reactions previously described in processes (a), (b), (c), (i) or (ii) are followed or preceded by one or more reactions known to the skilled of the art and are performed in an appropriate order to achieve the requisite substitutions on W, X, Y, R1, R2, R3 and R4 defined above to afford other compounds of formula (I). Non-limiting examples of such reactions whose conditions can be found in the literature include:

protection of reactive functions,
deprotection of reactive functions, halogenation,
dehalogenation,
dealkylation,
alkylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of esters groups,
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups,
S-oxidation,
N-oxidation,
salification.

The compounds of formula (III), (IV) and (V) are either known or may be prepared in accordance with known procedures such as those described herein.

It will be appreciated that certain intermediates used in the synthesis of the compound of formula (I) may constitute additional aspects of the invention. For example, according to a further aspect of the invention there is provided a compound of formula (II):

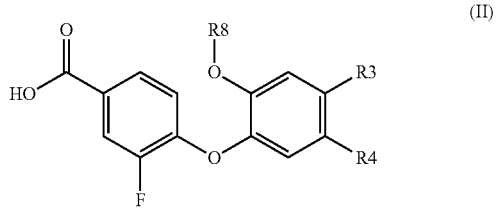

wherein R3 and R4 are as defined hereinbefore and R8 represents a protecting group;
or a salt or solvate thereof.

As illustrated by the examples given below, the hereinbefore disclosed compounds of formula (I) have valuable biological properties. They are particularly useful as antibacterial agents having a selective spectrum of activity in vitro and in vivo against bacterial strains relying on FabI and related targets. Such strains encompass *Staphylococcus aureus* including multiresistant strains (such as methicillin-susceptible *Staphylococcus aureus* (MSSA), methicillin-resistant *Staphylococcus aureus* (MRSA), vancomycin-intermediate *Staphylococcus aureus* (VISA) and vancomycin-resistant *Staphylococcus aureus* (VRSA) strains), *Acinetobacter baumannii, Bacillus anthracis, Chlamydophila pneumoniae, Escherichia coli, Haemophilus influenzae, Helicobacter pylori, Klebsiella pneumoniae, Neisseria meningitidis* and also bacteria such as *Mycobacterium tuberculosis* carrying homologous FabI enzymes such as InhA or other organisms such as *Plasmodium falciparum*. In one embodiment, the compound of the invention is used in the treatment of *Staphylococcus aureus* microbial infections including multiresistant strains such as methicillin-susceptible *Staphylococcus aureus* (MSSA), methicillin-resistant *Staphylococcus aureus* (MRSA), vancomycin-intermediate *Staphylococcus aureus* (VISA) and vancomycin-resistant *Staphylococcus aureus* (VRSA) strains.

The compounds of formula (I) are therefore particularly suitable as active principles of a medicament.

According to a further aspect of the invention, there is provided a compound of formula (I) as hereinbefore defined for use in therapy.

According to a further aspect of the invention, there is provided a pharmaceutical composition comprising a compound of formula (I) as hereinbefore defined, in association with a pharmaceutically acceptable excipient or carrier.

Said pharmaceutical compositions are advantageously formulated to be administered under oral, topical, parental including injectable routes, such as intravenous administration, with individual doses appropriate for the patient to be treated.

The compositions according to the invention can be solid, liquid or in the form of a gel/cream and be present in the pharmaceutical forms commonly used in human medicine, such as for example, plain or sugar-coated tablets, gelatin capsules, granules, suppositories, injectable preparations, ointments, creams, gels; they are prepared according to the customary methods. The active ingredient/s can be incorporated using excipients which are customarily used in these pharmaceutical compositions, such as talc, gum arabic, lactose, starch, magnesium stearate, aqueous or non-aqueous vehicles, fatty substances of animal or vegetable origin, paraffin derivatives, glycols, various wetting agents, dispersants or emulsifiers, preservatives. These compositions can also be present in the form of a powder intended to be dissolved extemporaneously in an appropriate vehicle, for example, non-pyrogenic sterile water.

The dose administered varies according to the condition treated, the patient in question, the administration route and the product envisaged. It can, for example, be comprised between 0.01 g and 10 g per day, by oral route or by intramuscular or intravenous route in humans.

Said compositions are particularly useful to treat human or animal infections by microbial pathogens such as *Staphylococcus aureus* including multiresistant strains, *Acinetobacter baumannii, Bacillus anthracis, Chlamydophila pneumoniae, Escherichia coli, Haemophilus influenzae, Helicobacter pylori, Klebsiella pneumoniae, Neisseria meningitidis, S. intermedius, P. multocida, B. bronchiseptica, M. haemolytica* and *A. pleuropneumoniae*. and also bacteria such as *Mycobacterium tuberculosis* or other organisms such as *Plasmodium falciparum*.

Said compositions can also be useful in multitherapy, in combination with other medicaments, for example with antibiotics. It will be appreciated that such multitherapy may typically comprise either a composition comprising the compound of formula (I) additionally comprising one or more other medicaments, such as antibiotics or co-administration (i.e. sequential or simultaneous administration).

The invention therefore also relates to a method of treatment of microbial infections which comprises administering to a patient in need thereof an efficient amount of a compound of formula (I) as hereinbefore defined.

The invention also relates to a compound of formula (I) as hereinbefore defined for use in the treatment of microbial infections.

The invention also relates to the use of a compound of formula (I) as hereinbefore defined in the manufacture of a medicament for the treatment of microbial infections.

The invention also relates to a pharmaceutical composition comprising a compound of formula (I) as hereinbefore defined for use in the treatment of microbial infections.

EXAMPLES

Proton nuclear magnetic resonance (¹H NMR) spectra were recorded on a 400 MHz Brüker instrument, and chemical shifts are reported in parts per million downfield from the internal standard tetramethylsilane (TMS). Abbreviations for NMR data are as follows: s=singlet, d=doublet, t=triplet, q=quadruplet, m=multiplet, dd=doublet of doublets, dt=doublet of triplets, br=broad. indicates the NMR coupling constant measured in Hertz. $CDCl_3$ is deuteriochloroform, DMSO-$d_6$ is hexadeuteriodimethylsulfoxide, and $CD_3OD$ is tetradeuteriomethanol. Mass spectra were obtained using electrospray ionization (ESI) techniques on an Agilent 1100 Series LCMS. Analtech Silica Gel GF and E. Merck Silica Gel 60 F-254 thin layer plates were used for thin layer chromatography. Flash chromatography was carried out on Flashsmart Pack cartridge irregular silica 40-60 μm or spherical silica 20-40 μm. Preparative thin layer chromatography was carried out on Analtech Silica Gel GF 1000 μm 20×20 cm.

The meaning of certain abbreviations is given herein. ESI refers to electrospray ionization, HPLC refers to high pressure liquid chromatography, LCMS refers to liquid chromatography coupled with a mass spectrometer, M in the context of mass spectrometry refers to the molecular peak, MS refers to mass spectrometer, NMR refers to nuclear magnetic resonance, pH refers to potential of hydrogen, TEA refers to triethylamine, DIPEA refers to N,N-diisopropylethylamine, HOBt refers to 1-hydroxybenzotriazole, DCM refers to dichloromethane, EtOAc refers to ethyl acetate, DMF refers to N,N-dimethylformamide, EDAC refers N-(3-dimethylaminopropyl)-N'-ethylcarbodiimide hydrochloride, DMAP or 4-DMAP refers to 4-(dimethylamino)pyridine, TLC refers to thin layer chromatography.

The starting materials are commercially available unless indicated otherwise.

Intermediate 1

4-(4-Ethyl-5-fluoro-2-methoxyphenoxy)-3-fluorobenzonitrile (D1)

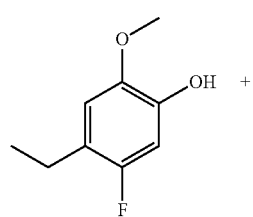

A suspension of 4-ethyl-5-fluoro-2-methoxyphenol (1 g, 5.87 mmol), 3,4-difluorobenzonitrile (899 mg, 6.46 mmol) and potassium hydroxide (395 mg, 7.04 mmol) in anhydrous acetonitrile (35 mL) under argon was stirred at 80° C. overnight. The reaction mixture was concentrated under vacuum and diluted with ethyl acetate and a saturated aqueous solution of ammonium chloride. The aqueous layer was separated and extracted twice with ethyl acetate. The combined organic phases were dried over sodium sulfate, filtrated and concentrated in vacuo to give a brown oil (1.6 g). The crude product was purified by flash chromatography on silica gel, using cyclohexane/ethyl acetate (9:1) as eluent. The title product was obtained as a colourless oil that crystallized slowly (1.42 g, 84%).

LCMS (ESI+) m/z 290 (M+H)⁺.

Intermediate 2

4-(4-Ethyl-5-fluoro-2-methoxyphenoxy)-3-fluorobenzoic acid (D2)

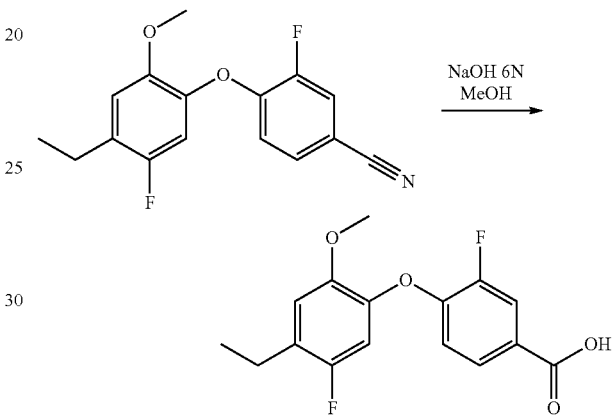

To a solution of 4-(4-ethyl-5-fluoro-2-methoxyphenoxy)-3-fluorobenzonitrile (420 mg, 1.45 mmol; which may be prepared as described in D1) in methanol (15 mL) was added an aqueous solution of 6N NaOH (7.3 mL, 43.6 mmol). The reaction mixture was heated to reflux (70° C.) and stirred overnight. After cooling with an ice bath, concentrated HCl (3.7 mL) was added slowly. The mixture was diluted with ethyl acetate and water. The aqueous layer was separated and extracted twice with ethyl acetate. The combined organic phases were dried over sodium sulfate, filtrated and concentrated in vacuo to give the title product as a beige solid (447 mg, quantitative).

LCMS (ESI−) m/z 307 (M−H)⁻.

Intermediate 3

4-[4-(4-Ethyl-5-fluoro-2-methoxyphenoxy)-3-fluorobenzoyl]piperazin-2-one (D3)

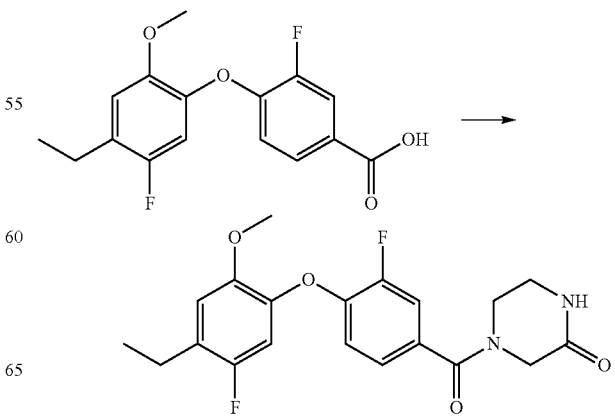

To a solution of 4-(4-ethyl-5-fluoro-2-methoxyphenoxy)-3-fluorobenzoic acid (55 mg, 0.18 mmol; which may be prepared as described in D2) in dichloromethane (1.8 mL) under Argon cooled at 0° C. were added oxalyl chloride (2M in dichloromethane, 135 μL, 0.27 mmol) and a drop of N,N-dimethylformamide. The mixture was allowed to come to room temperature over 2 hours, and then piperazin-2-one (20 mg, 0.20 mmol) followed by diisopropylethylamine (93 μL, 0.53 mmol) were added. The reaction mixture was cooled to 0° C. and a solution of 1N HCl was added. After stirring a few minutes, dichloromethane was added and the aqueous layer (pH 7) was extracted twice with dichloromethane. The combined organic phases were dried over sodium sulfate, filtrated and concentrated in vacuo. The residue was purified by preparative thin layer chromatography on silica gel, using dichloromethane/methanol (95:5) as eluent. The title product was obtained as a yellow oil (38 mg, 55%).

LCMS (ESI+) m/z 391 (M+H)+, 413 (M+Na)+.

Example 1

4-[4-(4-Ethyl-5-fluoro-2-hydroxyphenoxy)-3-fluorobenzoyl]piperazin-2-one (E1)

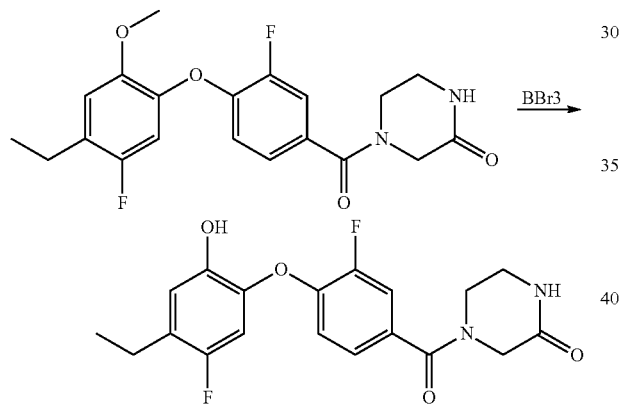

To a solution of 4-[4-(4-ethyl-5-fluoro-2-methoxyphenoxy)-3-fluorobenzoyl]piperazin-2-one (38 mg, 0.10 mmol; which may be prepared as described in D3) in dichloromethane (300 μL) under Argon cooled at −30° C. was added dropwise boron tribromide (1M in dichloromethane, 273 μL, 0.27 mmol). The mixture was allowed to come to room temperature and after stirring 20 h, was diluted with dichloromethane. The mixture was quenched carefully at 0° C. with an aqueous saturated solution of ammonium chloride and then diluted with ethyl acetate. The aqueous layer was extracted twice with ethyl acetate and the combined organic phases were washed with brine, dried over sodium sulfate, filtrated and concentrated in vacuo. The residue was purified by preparative thin layer chromatography on silica gel, using dichloromethane/methanol (95:5) as eluent. The title product was obtained as a white solid (32 mg, 86%).

LCMS (ESI−) m/z 355 (M−HF−H)−, 375 (M−H)−.

$^1$H NMR (400 MHz, DMSO-d$_6$), δ (ppm): 9.60 (s, 1H), 8.12 (s, 1H), 7.46 (dd, J=2.0, 11.2 Hz, 1H), 7.20 (d, J=8.6 Hz, 1H), 6.97 (d, J=10.2 Hz, 1H), 6.87 (d, J=7.9 Hz, 1H), 6.79 (t, J=8.4 Hz, 1H), 4.01 (br s, 2H), 3.58 (br s, 2H), 3.23 (s, 2H), 2.56 (q, J=7.2 Hz, 2H), 1.16 (t, J=7.5 Hz, 3H).

Example 2

4-[4-(4-Ethyl-2-hydroxyphenoxy)-3-fluorobenzoyl]piperazin-2-one (E2)

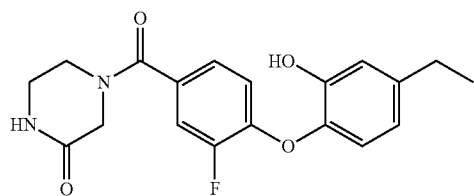 [SMILES: CCc1ccc(Oc2ccc(C(=O)N3CCNC(=O)C3)cc2F)c(O)c1]

The compound of Example 2 (E2) was prepared in an analogous manner to that described in Example 1 (E1) to obtain the title compound as a white solid with a 50% overall yield.

LCMS (ESI+) m/z 359 (M+H)+.

$^1$H NMR (400 MHz, DMSO-d$_6$), δ (ppm): 9.61 (s, 1H), 8.12 (s, 1H), 7.44 (dd, J=1.9, 11.3 Hz, 1H), 7.18 (d, J=8.5 Hz, 1H), 6.96 (d, J=8.2 Hz, 1H), 6.83 (d, J=1.9 Hz, 1H), 6.70 (m, 2H), 4.04-3.96 (m, 2H), 3.70-3.50 (m, 2H), 3.26-3.20 (m, 2H), 2.54 (q, J=7.6 Hz, 2H), 1.17 (t, J=7.6 Hz, 3H)

Example 3

4-Fluoro-2-{2-fluoro-4-[(3-oxopiperazin-1-yl)carbonyl]phenoxy}-5-ethylphenyl ethyl carbonate (E3)

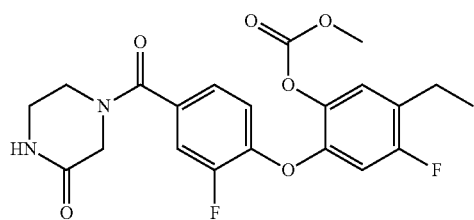 [SMILES: CCc1cc(OC(=O)OC)c(Oc2ccc(C(=O)N3CCNC(=O)C3)cc2F)cc1F]

To a solution of 4-[4-(4-ethyl-5-fluoro-2-hydroxyphenoxy)-3-fluorobenzoyl]piperazin-2-one (20 mg, 0.053 mmol; which may be prepared as described in D3) in acetonitrile (550 μL) was added KOH (3 mg, 0.053 mmol) followed by ethylchlorocarbonate (6 μL, 0.058 mmol). After 1 hour at room temperature, the mixture was quenched with water. The aqueous layer was extracted twice with ethyl acetate. The organic phase was dried over sodium sulphate, filtered and concentrated under vacuum. The residue was purified by preparative thin layer chromatography on silica gel, using dichloromethane/methanol (95:5) as eluent. The title product was obtained as a white solid (11 mg, 46%).

LCMS (ESI+) m/z 449 (M+H)+.

$^1$H NMR (400 MHz, DMSO-d$_6$), δ (ppm): 8.13 (m, 1H), 7.52 (dd, J=1.9, 11.0 Hz, 1H), 7.40 (d, J=7.6 Hz, 1H), 7.26 (d, J=8.4 Hz, 1H), 7.15-7.04 (m, 2H), 4.19 (q, J=7.1 Hz, 2H), 4.08-3.95 (m, 2H), 3.91-3.46 (m, 2H), 3.26-3.21 (m, 2H), 2.50 (q, J=7.3 Hz, 2H), 1.20 (m, 6H)

Example 4

4-[4-(4-Ethyl-5-fluoro-2-hydroxyphenoxy)-3-fluorobenzoyl]piperazine-2,6-dione (E4)

Step 1: 4-Benzylpiperazine-2,6-dione

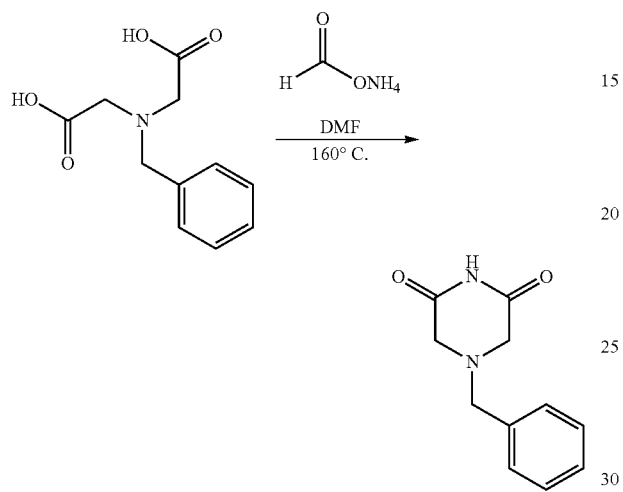

A suspension of 2,2'-(benzylazanediyl)diacetic acid (5.0 g, 22.4 mmol) and ammonium formate (4.2 g, 67.2 mmol) in N,N-dimethylformamide (75 mL) was stirred to reflux (160° C.) for 2 days. After cooling to room temperature, the reaction mixture was diluted by successive addition of ethyl acetate (150 mL) and a saturated solution of sodium hydrogen carbonate (150 mL). The aqueous layer was extracted with ethyl acetate (2×150 mL) and the combined organic phases were washed with a saturated solution of sodium chloride (3×100 mL), dried over sodium sulfate, filtered and concentrated under vacuum to give the title product as a yellow liquid (3.96 g, 87%).

LCMS (ESI-APCI) m/z 205 (M+H)+

$^1$H NMR (CDCl$_3$, 400 MHz): δ (ppm): 8.49 (br s, NH), 7.37-7.27 (m, 5H), 3.67 (s, 2H), 3.37 (s, 4H).

Step 2: piperazine-2,6-dione hydrochloride

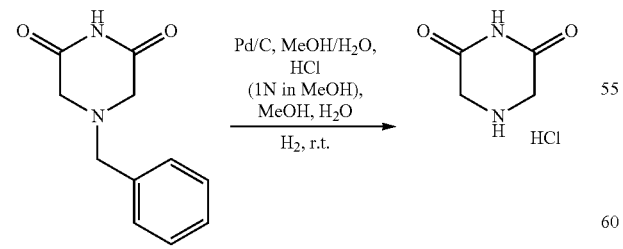

To a solution of 4-benzylpiperazine-2,6-dione (which may be prepared in accordance with the experimental described in Example 4, step 1; 2.0 g, 9.8 mmol) in a mixture of methanol/H$_2$O (65 mL/28 mL) were added a solution of HCl 1N in methanol (23.8 mL) and Pd/C (10% wet, 0.2% wt., 400 mg).

The reaction mixture was degassed 3 times with hydrogen/vacuum prior to its overnight stirring under hydrogen (P=1 atm). The reaction mixture was then filtered on Clarcel® and washed with methanol. The filtrate was finally concentrated to dryness and the residue was precipitated from a mixture of methanol and ether. The title product was obtained as a beige solid (418 mg, 28%).

LCMS (ESI-APCI) m/z 115 (M+H)+

$^1$H NMR (DMSO-d$_6$, 400 MHz): δ (ppm): 11.80 (s, 1H), 10.56 (br s, 2H), 3.94 (s, 4H).

Step 3: 4-(4-Ethyl-5-fluoro-2-methoxyphenoxy)-3-fluorobenzonitrile

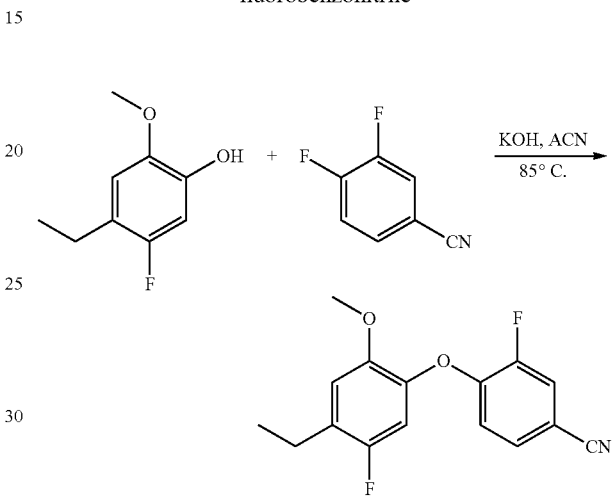

Potassium hydroxide (2.4 g, 43.13 mmol) was added to a solution of 4-ethyl-5-fluoro-2-methoxyphenol (6.1 g, 35.94 mmol) and 3,4-difluorobenzonitrile (5.0 g, 35.94 mmol) in anhydrous acetonitrile (80 mL). The reaction mixture was stirred at 85° C. overnight then concentrated under vacuum. The residue was solubilized in ethyl acetate (300 mL) and diluted by addition of a saturated solution of ammonium chloride (200 mL). The aqueous layer was separated and extracted with ethyl acetate (2×200 mL). The combined organic phases were dried over sodium sulfate, filtered and concentrated to dryness to give a brown solid. After trituration in pentane, the title product was obtained as a brown solid (8.10 g, 77%).

$^1$H NMR (CDCl$_3$, 400 MHz): δ (ppm): 7.45 (dd, J=2.0, 10.4 Hz, 1H), 7.32 (td, J=1.6, 3.2, 8.8 Hz, 1H), 6.85-6.77 (m, 3H), 3.77 (s, 3H), 2.69 (q, J=7.6 Hz, 2H), 1.27 (t, J=7.6 Hz, 3H).

Step 4: 4-(4-Ethyl-5-fluoro-2-methoxyphenoxy)-3-fluorobenzoic acid

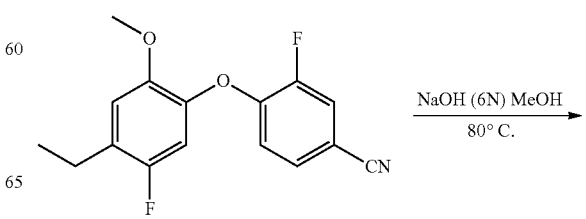

-continued

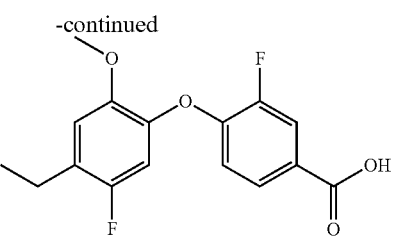

An aqueous solution of NaOH 6N (70 mL, 420 mmol) was added to a solution of 4-(4-ethyl-5-fluoro-2-methoxyphenoxy)-3-fluorobenzonitrile (which may be prepared in accordance with the experimental described in Example 4, step 3; 4.0 g, 13.82 mmol) in methanol (140 mL). The reaction mixture was then stirred at reflux (80° C.) overnight. After cooling to 0° C., the reaction mixture was acidified by slow addition of concentrated HCl (25 mL) until pH=2. The mixture was then diluted by addition of ethyl acetate (300 mL) and the aqueous layer was separated and extracted with ethyl acetate (2×200 mL). The combined organic phases were dried over sodium sulfate, filtered and concentrated under vacuum to afford the title product as a beige solid (4.20 g, quantitative).

$^1$H NMR (DMSO-$d_6$, 400 MHz): 13.1 (br s, OH), 7.77 (d, J=11.6 Hz, 1H), 7.70 (d, J=8.4 Hz, 1H), 7.14 (m, 2H), 6.79 (m, 1H), 3.72 (s, 3H), 2.63 (q, J=7.6 Hz, 2H), 1.27 (t, J=7.6 Hz, 3H).

Step 5: 4-[4-(4-Ethyl-5-fluoro-2-methoxyphenoxy)-3-fluorobenzoyl]piperazine-2,6-dione

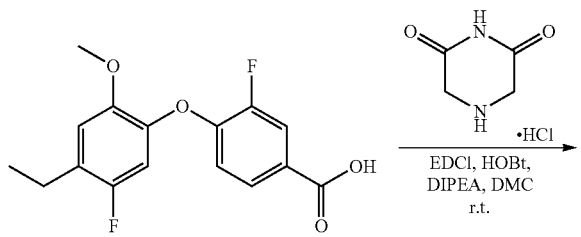

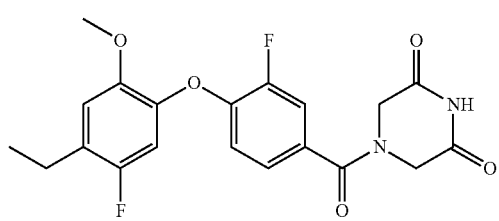

N,N-Diisopropylethylamine (0.29 mL, 1.7 mmol), piperazine-2,6-dione hydrochloride (88 mg, 0.58 mmol), EDCI (112 mg, 0.58 mmol) and HOBt (79 mg, 0.58 mmol) were successively added to a solution of 4-(4-ethyl-5-fluoro-2-methoxyphenoxy)-3-fluorobenzoic acid (which may be prepared in accordance with the experimental described in Example 4, step 4; 150 mg, 0.48 mmol) in dichloromethane (1.6 mL). The reaction mixture was stirred at room temperature overnight then diluted by addition of dichloromethane (20 mL) and a saturated solution of ammonium chloride (20 mL). After separation, the aqueous layer was extracted with dichloromethane (2×20 mL). The combined organic phases were washed with a saturated solution of sodium hydrogen carbonate (20 mL), dried over sodium sulfate, filtered and concentrated under vacuum. The residue was purified by chromatography on silica gel, using dichloromethane/methanol (95:5 to 90:10) as eluent. The title product was obtained as a beige solid (130 mg, 66%).

$^1$H NMR (CDCl$_3$, 400 MHz): δ (ppm): 8.21 (br s, NH), 7.30 (dd, J=1.6, 10.4 Hz, 1H), 7.12 (d, J=8.4 Hz, 1H), 6.85-6.78 (m, 3H), 4.50 (s, 4H), 3.80 (s, 3H), 2.68 (q, J=7.6 Hz, 2H), 1.27 (t, J=7.6 Hz, 3H).

Step 6: 4-[4-(4-Ethyl-5-fluoro-2-hydroxyphenoxy)-3-fluorobenzoyl]piperazine-2,6-dione

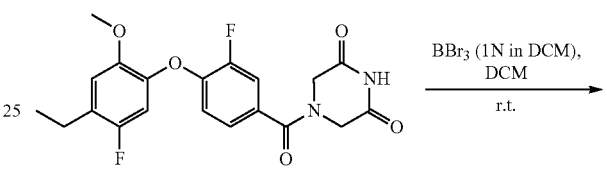

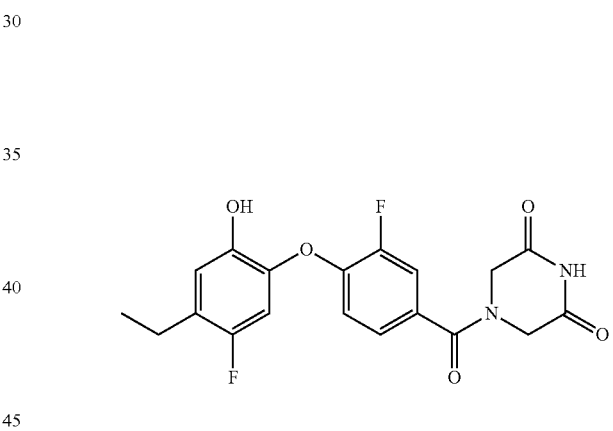

A commercial solution of boron tribromide (1N in DCM, 0.4 mL, 0.4 mmol) was added to a solution of 4-[4-(4-ethyl-5-fluoro-2-methoxyphenoxy)-3-fluorobenzoyl]piperazine-2,6-dione (which may be prepared in accordance with the experimental described in Example 4, step 5; 60 mg, 0.15 mmol) in dichloromethane (0.5 mL) placed under argon at −30° C. The reaction mixture was stirred at room temperature overnight and then diluted by addition of dichloromethane (10 mL) and a saturated solution of ammonium chloride (10 mL). After separation, the aqueous layer was extracted with dichloromethane (2×10 mL). The combined organic phases were dried over sodium sulfate, filtered and concentrated under vacuum. The residue was purified by chromatography on silica gel, using dichloromethane/methanol (98:2) as eluent. The title product was obtained as a white solid (35 mg, 60%).

$^1$H NMR (DMSO-$d_6$, 400 MHz): δ (ppm): 11.43 (br s, OH), 9.61 (br s, NH), 7.49 (d, J=11.2 Hz, 1H), 7.21 (d, J=8.0 Hz, 1H), 7.00 (d, J=10.0 Hz, 1H), 6.87 (d, J=7.2 Hz, 1H), 6.80

(dd, J=7.6, 8.4 Hz, 1H), 4.32 (s, 4H), 2.55 (q, 2H), 1.16 (t, J=7.6 Hz, 3H). The quadruplet CH$_2$ is partially hidden by the DMSO signal.

Example 5
4-[4-(4-Ethyl-5-fluoro-2-hydroxyphenoxy)-3-fluorobenzoyl]-1-methylpiperazin-2-one (E5)
Step 1: 4-[4-(4-Ethyl-5-fluoro-2-methoxyphenoxy)-3-fluorobenzoyl]piperazin-2-one

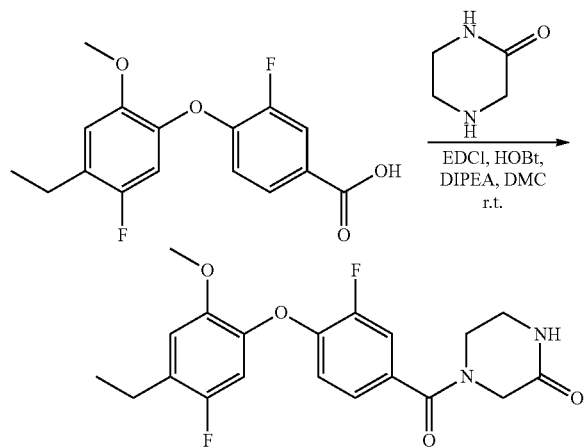

N,N-Diisopropylethylamine (2.8 mL, 16 mmol), piperazin-2-one (780 mg, 7.8 mmol), EDCI (1.5 g, 7.8 mmol) and HOBt (1.05 g, 7.8 mmol) were successively added to a solution of 4-(4-ethyl-5-fluoro-2-methoxyphenoxy)-3-fluorobenzoic acid (which may be prepared in accordance with the experimental described in Example 4, step 4; 2.0 g, 6.5 mmol) in dichloromethane (22 mL). The reaction mixture was stirred at room temperature overnight and then diluted by addition of dichloromethane (50 mL) and a saturated solution of sodium hydrogen carbonate (50 mL). After separation, the aqueous layer was extracted with dichloromethane (2×50 mL). The combined organic phases were dried over sodium sulfate, filtered and concentrated under vacuum. The residue was purified by chromatography on silica gel, using dichloromethane/petroleum ether (80/20) to dichloromethane (100%) to dichloromethane/methanol (98:2 to 95:5) as eluent. The title product was obtained as a yellow solid (2.0 g, 80%).

LCMS (ESI-APCI) m/z 391 (M+H)$^+$ $^1$H NMR (CDCl$_3$, 400 MHz): δ (ppm): 7.30 (d, J=10.8 Hz, 1H), 7.13 (d, J=8.8 Hz, 1H), 6.84 (m, 2H), 6.74 (d, J=9.6 Hz, 1H), 6.40 (br s, NH), 4.27 (br s, 2H), 3.86 (br s, 2H), 3.81 (s, 3H), 3.48 (br s, 2H), 2.67 (q, J=7.6 Hz, 2H), 1.26 (t, J=7.6 Hz, 3H).

Step 2: 4-[4-(4-Ethyl-5-fluoro-2-methoxyphenoxy)-3-fluorobenzoyl]-1-methylpiperazin-2-one

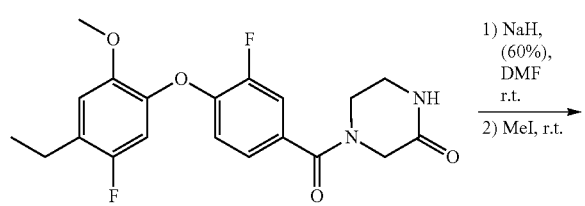

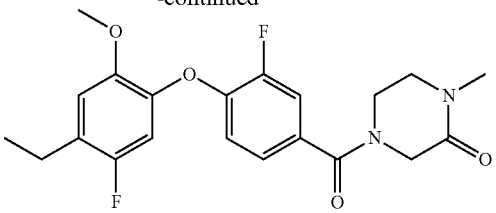

Sodium hydride (60% in oil, 25 mg, 0.6 mmol) was added to a solution of 4-[4-(4-ethyl-5-fluoro-2-methoxyphenoxy)-3-fluorobenzoyl]-piperazin-2-one (which may be prepared in accordance with the experimental described in Example 5, step 1; 200 mg, 0.5 mmol) in N,N-dimethylformamide (5 mL). The reaction mixture was stirred at room temperature for 15 minutes prior to the addition of iodomethane (0.48 mL, 0.77 mmol). After stirring at room temperature for 1 hour, the reaction mixture was diluted by addition of ethyl acetate (30 mL) and water (30 mL). The two phases were separated and the aqueous layer was extracted with ethyl acetate (2×30 mL). The combined organic phases were finally washed with a saturated solution of sodium chloride (5×20 mL), dried over sodium sulfate, filtered and concentrated under vacuum to afford the title product as a yellow oil (200 mg, 97%).

LCMS (ESI-APCI) m/z 405 (M+H)$^+$ $^1$H NMR (CDCl$_3$, 400 MHz): δ (ppm): 7.30 (dd, J=1.6, 10.4 Hz, 1H), 7.13 (d, J=8.4 Hz, 1H), 6.83 (m, 2H), 6.74 (d, J=9.6 Hz, 1H), 4.25 (br s, 2H), 3.92 (br s, 2H), 3.81 (s, 3H), 3.44 (br s, 2H), 3.00 (s, 3H), 2.67 (q, J=7.6 Hz, 2H), 1.27 (t, J=7.6 Hz, 3H).

Step 3: 4-[4-(4-Ethyl-5-fluoro-2-hydroxyphenoxy)-3-fluorobenzoyl]-1-methylpiperazin-2-one

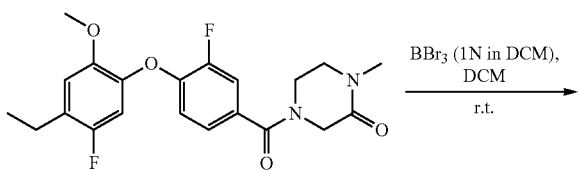

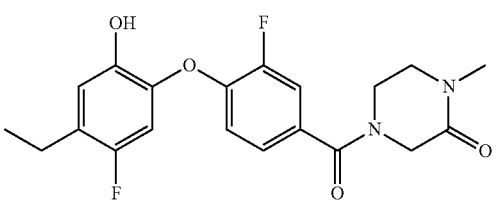

A commercial solution of boron tribromide (1N in DCM, 1.33 mL, 1.32 mmol) was added to a solution of 4-[4-(4-ethyl-5-fluoro-2-methoxyphenoxy)-3-fluorobenzoyl]-1-methylpiperazin-2-one (which may be prepared in accordance with the experimental described in Example 5, step 2; 200 mg, 0.49 mmol) in dichloromethane (1.6 mL) placed under argon at −30° C. The reaction mixture was stirred at room temperature overnight and diluted by addition of dichloromethane (30 mL) and a saturated solution of ammonium chloride (30 mL). After separation, the aqueous layer was extracted with dichloromethane (2×30 mL). The combined organic phases were dried over sodium sulfate, filtered and concentrated under vacuum. The residue was purified by chromatography on silica gel, using dichloromethane/methanol (95:5) as eluent. The title product was obtained as a yellow solid (135 mg, 70%).

LCMS (ESI-APCI) m/z 391 (M+H)+

1H NMR (CDCl3, 400 MHz): δ (ppm): 7.33 (dd, J=1.2, 10.4 Hz, 1H), 7.20 (d, J=8.4 Hz, 1H), 7.05 (t, J=8.4 Hz, 1H), 6.90 (d, J=7.6 Hz, 1H), 6.58 (d, J=9.6 Hz, 1H), 5.4 (br s, OH), 4.24 (br s, 2H), 3.94 (br s, 2H), 3.46 (br s, 2H), 3.03 (s, 3H), 2.62 (q, J=7.6 Hz, 2H), 1.23 (t, J=7.6 Hz, 3H).

mmol). After stirring for 2 days at room temperature, the reaction mixture was diluted by addition of ethyl acetate (20 mL) and water (20 mL). After separation, the aqueous layer was extracted with ethyl acetate (2×20 mL). The combined organic phases were washed with a saturated solution of sodium chloride (2×20 mL), dried over sodium sulfate, filtered and concentrated under vacuum. The residue was purified by chromatography on silica gel, using dichloromethane/methanol (98:2 to 95:5) as eluent. The title product was obtained as a white solid (300 mg, 65%).

LCMS (ESI-APCI) m/z 448 (M+H)+

1H NMR (CDCl3, 400 MHz): δ (ppm): 7.31 (d, J=10.4 Hz, 1H), 7.14 (d, J=7.6 Hz, 1H), 6.84 (m, 2H), 6.74 (d, J=7.6 Hz, 1H), 6.10 and 5.53 (br s, NH2), 4.33 (br s, 2H), 4.06 (br s, 2H), 3.93 (br s, 2H), 3.80 (s, 3H), 3.59 (br s, 2H), 2.67 (q, J=7.6 Hz, 2H), 1.26 (t, J=7.6 Hz, 3H).

Step 2: 2-[4-(4-(4-Ethyl-5-fluoro-2-hydroxyphenoxy)-3-fluorobenzoyl]-2-oxopiperazin-1-yl)acetamide

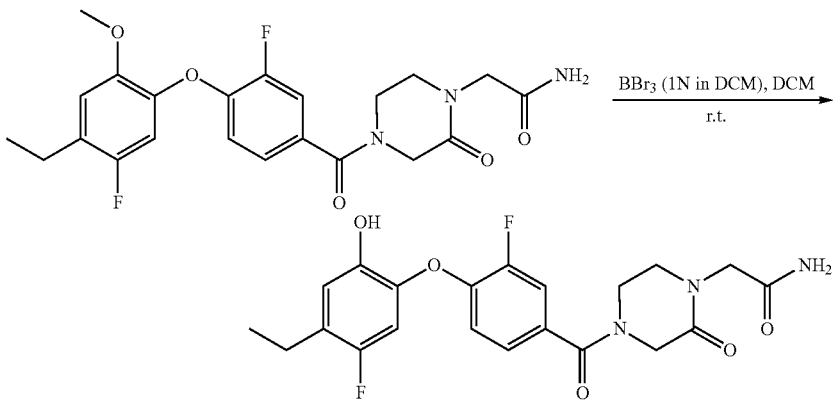

Example 6

2-[4-(4-(4-Ethyl-5-fluoro-2-hydroxyphenoxy)-3-fluorobenzoyl]-2-oxopiperazin-1-yl)acetamide (E6)

Step 1: 2-[4-(4-(4-Ethyl-5-fluoro-2-methoxyphenoxy)-3-fluorobenzoyl]-2-oxopiperazin-1-yl)acetamide

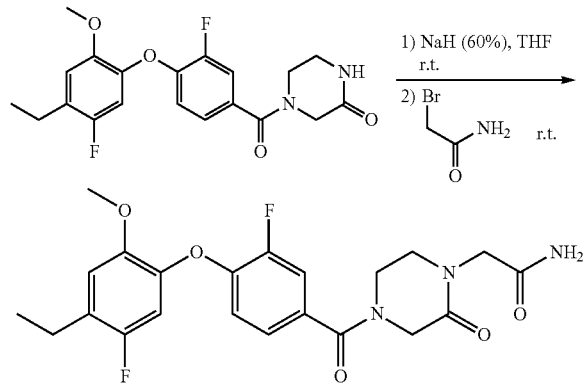

Sodium hydride (60% in oil, 49 mg, 1.2 mmol) was added to a solution of 4-[4-(4-ethyl-5-fluoro-2-methoxyphenoxy)-3-fluorobenzoyl]-piperazin-2-one (which may be prepared in accordance with the experimental described in Example 5, step 1; 400 mg, 1 mmol) in tetrahydrofuran (10 mL). The reaction mixture was stirred at room temperature for 15 minutes prior to the addition of 2-bromoacetamide (212 mg, 1.5

A commercial solution of boron tribromide (1N in DCM, 0.84 mL, 0.84 mmol) was added to a solution of 2-[4-(4-(4-ethyl-5-fluoro-2-methoxyphenoxy)-3-fluorobenzoyl]-2-oxopiperazin-1-yl)acetamide (which may be prepared in accordance with the experimental described in Example 6, step 1; 140 mg, 0.31 mmol) in dichloromethane (1 mL) placed under argon at −30° C. The reaction mixture was stirred at room temperature overnight and diluted by addition of dichloromethane (20 mL) and a saturated solution of ammonium chloride (20 mL). After separation, the aqueous layer was extracted with dichloromethane (2×20 mL). The combined organic phases were dried over sodium sulfate, filtered and concentrated under vacuum. The residue was purified by chromatography on silica gel, using dichloromethane/methanol (95:5 to 90:10) as eluent. The title product was obtained as a white solid (30 mg, 22%).

LCMS (ESI+) m/z 434 (M+H)+

1H NMR (DMSO-d6, 400 MHz): δ (ppm): 9.65 (br s, OH), 7.45 (d, J=8.4 Hz, 1H), 7.44 and 7.12 (br s, NH2), 7.22 (d, J=8.4 Hz, 1H), 6.97 (d, J=10 Hz, 1H), 6.87 (d, J=7.6 Hz, 1H), 6.81 (dd, J=8, 8.4 Hz, 1H), 4.12 (br s, 2H), 3.92 (s, 2H), 3.72

(br s, 2H), 3.40 (br s, 2H), 2.56 (q, J=7.6 Hz, 2H), 1.17 (t, J=7.6 Hz, 3H). The quadruplet CH$_2$ is hidden partially by the DMSO signal.

Example 7

4-[4-(4-Ethyl-5-fluoro-2-hydroxyphenoxy)-3-fluorobenzoyl]-1-(morpholinomethyl)piperazin-2-one (E7)

Step 1: 4-[4-(4-Ethyl-5-fluoro-2-hydroxyphenoxy)-3-fluorobenzoyl]-piperazin-2-one

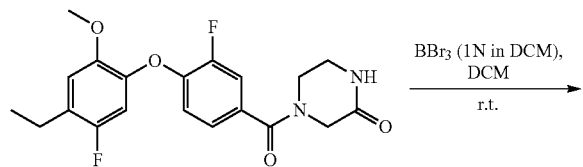

A commercial solution of boron tribromide (1N in DCM, 3.5 mL, 3.46 mmol) was added to a solution of 4-[4-(4-ethyl-5-fluoro-2-methoxyphenoxy)-3-fluorobenzoyl]piperazin-2-one (which may be prepared in accordance with the experimental described in Example 5, step 1; 500 mg, 1.28 mmol) in dichloromethane (4.3 mL) placed under argon at −30° C. The reaction mixture was stirred at room temperature for 36 hours then diluted by addition of dichloromethane (20 mL) and water (20 mL). After separation, the aqueous layer was extracted with dichloromethane (2×20 mL). The combined organic phases were dried over sodium sulfate, filtered and concentrated under vacuum. The residue was purified by chromatography on silica gel, using dichloromethane/acetone (80:20) as eluent. The title product was obtained as a beige solid (440 mg, 92%).

LCMS (ESI-APCI) m/z 377 (M+H)$^+$ $^1$H NMR (CDCl$_3$, 400 MHz): δ (ppm): 7.32 (d, J=10 Hz, 1H), 7.19 (d, J=8.4 Hz, 1H), 7.04 (t, 8.4 Hz, 1H), 6.90 (d, J=7.2 Hz, 1H), 6.60 (d, J=10 Hz, 1H), 6.30 (br s, NH), 4.26 (br s, 2H), 3.87 (br s, 2H), 3.48 (br s, 2H), 2.62 (q, J=7.6 Hz, 2H), 1.25 (t, J=7.6 Hz, 3H).

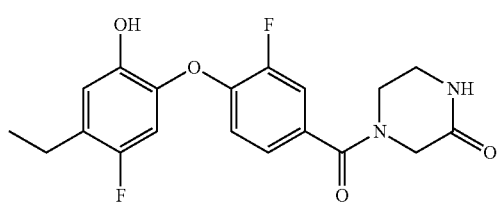

Step 2: 4-[4-(4-Ethyl-5-fluoro-2-hydroxyphenoxy)-3-fluorobenzoyl]-1-(morpholinomethyl)piperazin-2-one

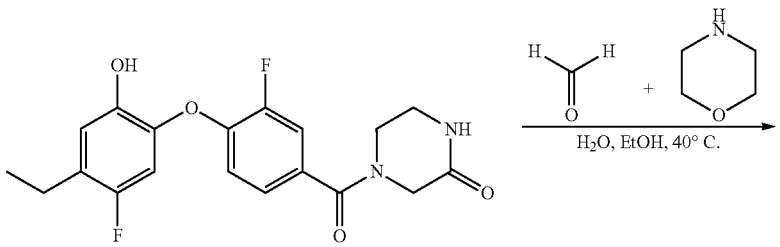

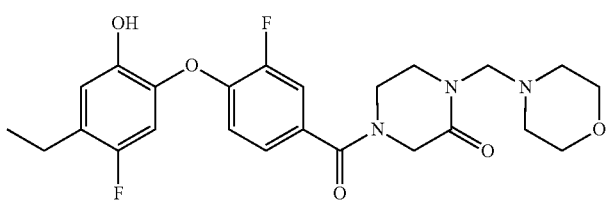

Formaldehyde (37% in water, 30 μL, 0.32 mmol) and morpholine (28 μL, 0.32 mmol) were successively added to a solution of 4-[4-(4-ethyl-5-fluoro-2-hydroxyphenoxy)-3-fluorobenzoyl]-piperazin-2-one (which may be prepared in accordance with the experimental described in Example 7, step 1; 100 mg, 0.26 mmol) in a mixture of methanol/H$_2$O (0.8 mL/0.8 mL). The mixture was stirred at 40° C. for 2 hours prior to the addition of more formaldehyde (37% in water, 30 μL, 0.4 mmol) and more morpholine (32 μL, 0.4 mmol). The reaction mixture was then stirred at 40° C. for two days. The reaction mixture was diluted by addition of ethyl acetate (20 mL) and water (20 mL). After separation, the aqueous layer was extracted with ethyl acetate (2×20 mL). The combined organic phases were dried over sodium sulfate, filtered and concentrated under vacuum. The residue was purified by chromatography on silica gel, using dichloromethane/methanol (98:2 to 96:4) as eluent. The title product was obtained as a white solid (55 mg, 44%).

LCMS (ESI-APCI) m/z 476 (M+H)$^+$ $^1$H NMR (DMSO-d$_6$, 400 MHz): δ (ppm): 9.59 (s, OH), 7.47 (dd, J=1.6, 11.6 Hz, 1H), 7.20 (d, J=8.4 Hz, 1H), 6.96 (d, J=10 Hz, 1H), 6.87 (d, J=7.6 Hz, 1H), 6.80 (t, J=8.4 Hz, 1H), 4.10 (br s, 2H), 4.03 (s, 2H), 3.67 (br s, 2H), 3.54 (m, 4H), 3.44 (m, 2H), 2.55 (q, J=7.6 Hz, 2H), 2.42 (m, 2H), 1.16 (t, J=7.6 Hz, 3H). The quadruplet CH$_2$ is partially hidden by the DMSO signal.

Example 8

4-[4-(4-Ethyl-5-fluoro-2-hydroxyphenoxy)-3-fluorobenzoyl]-3-methyl piperazin-2-one (E8)

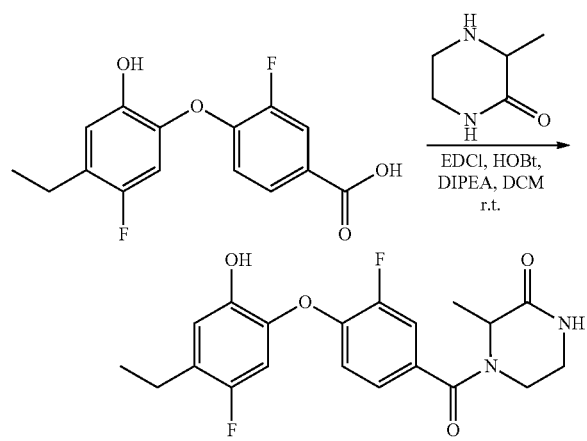

N,N-Diisopropylethylamine (74 μL, 0.42 mmol), 3-methylpiperazin-2-one (23.3 mg, 0.20 mmol), EDCI (39.1 mg, 0.20 mmol) and HOBt (27.6 g, 0.20 mmol) were successively added to a suspension of 4-(4-ethyl-5-fluoro-2-methoxyphenoxy)-3-fluorobenzoic acid (which may be prepared in accordance with the experimental described in Example 4, step 4; 50 mg, 0.17 mmol) in dichloromethane (0.55 mL). The reaction mixture was stirred at room temperature overnight then diluted by addition of dichloromethane (10 mL) and water (10 mL). After separation, the organic layer was washed with water (10 mL). The organic phase was dried over sodium sulfate, filtered and concentrated under vacuum. The residue was purified by chromatography on silica gel, using dichloromethane/methanol (98:2 to 95:5) as eluent. The title product was obtained as a white solid (24 mg, 36%).

LCMS (ESI-APCI) m/z 391 (M+H)$^+$ $^1$H NMR (acetone-d$_6$, 400 MHz): δ (ppm): 8.47 (br s, OH), 7.39 (dd, J=1.6, 11.2 Hz, 1H), 7.24 (d, J=8.4 Hz, 1H), 7.11 (br s, NH), 6.93 (m, 2H), 6.83 (d, J=10.0 Hz, 1H), 4.67 and 4.01 (br s, 2H), 3.50 (m, 2H), 3.30 (m, 1H), 2.61 (q, J=7.6 Hz, 2H), 1.44 (d, J=7.2 Hz, 3H), 1.20 (t, J=7.6 Hz, 3H).

Assay Data

1. FabI Inhibition

The compounds of the invention are useful inhibitors of bacterial FabI enzyme.

Compound inhibitory activity of FabI enzyme is measured in vitro by the IC$_{50}$ determination using a fluorescence based assay.

The protein FabI from *S. aureus* is prepared and purified using standard methods for recombinant protein expression after cloning of the gene in a prokaryotic expression vector.

The biochemical activity of the FabI enzyme is assessed using the following method.

The assay buffer "AB" contained 50 mM ADA (N-(2-acetamido)iminodiacetic acid monosodium salt) pH 6.5, 1 mM dithiothreitol, 0.006% Triton-X100 and 50 mM NaCl. The following components are added in a white polystyrene Costar plate (Ref 3912) up to a final volume of 55.5 μL: 1.5 μL DMSO or inhibitor dissolved in DMSO and 54 μL of a FabI/NADPH/NADP+ mixture in AB. After 60 min of pre-incubation at room temperature, the reaction is started by addition of 5 μL of trans-2-octenoyl N-acetylcysteamine thioester (t-o-NAC) to a final volume of 60.5 μL. This reaction mixture is then composed of 2 nM FabI, 40 μM NADPH (Sigma, N7505), 10 μM NADP+ (Sigma, N5755), 100 μM t-O-NAC and compound at defined concentration. Fluorescence intensity of NADPH (λex=360 nm, λem=520 nm) is measured immediately after t-O-NAC addition (T0), and approximately 50 min later (T50) by a Fluostar Optima (BMG) so as to achieve ±30% of NADPH conversion. Enzyme activity is calculated by first subtracting T0 signal to T50 and then subtracting background signal (FabI=0). Percentages of inhibition are calculated against untreated samples (Inhibitor=0) and IC$_{50}$ are fitted to a classical Langmuir equilibrium model using XLFIT (IDBS).

TABLE 1

In vitro inhibition of recombinant *S. aureus* FabI enzyme by selected compounds

| Example | FabI Inhibition IC$_{50}$ (μM) |
| --- | --- |
| 1 | 0.016 |
| 2 | 0.029 |
| 3 | 5 |

2. Antibacterial Activity

The compounds of the invention are useful antibacterial agents having a selective spectrum of activity in vitro against bacterial strains relying on FabI and related targets. Notably the compounds of the invention show activity against *Staphylococcus aureus* including multiresistant strains. The activity is presented as Minimum Inhibitory Concentration (MIC) expressed in μg/ml and was determined using broth microdilution or Agar dilution methods.

Strains

Antibacterial activity was determined on MSSA CIP 54.146 provided by the Centre de Ressources Biologiques de l'Institut Pasteur. Antibacterial activity was also determined on MRSA (IHMA #510059) and MSSA (IHMA #555189).

MIC Determination Using Broth Microdilution Method

This protocol is compliant with Clinical Laboratory Standards Institute (CLSI) methodology as described in M7-A7 document of the CLSI. The compound to be tested is diluted according to a geometric series of reason 2 in pure DMSO. Dilutions are transferred in sterile polystyrene microplates, followed by mid-log phase bacteria in cation-adjusted Muller-Hinton broth (ca-MHB, Fluka, Reference 90922) with a final inoculum of $5 \times 10^5$ cfu/ml. Microplates are incubated overnight at 35° C. MIC is defined as the lowest concentration of antimicrobial agent that completely prevents visible bacterial growth. All manipulations, but compound handling (in pure DMSO), are performed under sterile conditions. The final concentration of DMSO in the plates is 2%.

In order to evaluate the serum binding of test compounds, MICs were also measured in ca-MHB supplemented with 80% human serum (HS, Sigma, Reference H4522).

TABLE 2

Representative Examples of MIC (µg/ml) (Broth microdilution) by selected compounds of formula (I):

| Example | S. aureus CIP 54.146 | S. aureus CIP 54.146 in the presence of 80% human serum |
|---|---|---|
| 1 | 0.25 | 0.5 |
| 2 | 1 | 1 |

MIC Determination Using Susceptibility Method

Minimum inhibitory concentrations (MICs) were determined by broth microdilution according to CLSI guidelines (CLSI, M100-20[1], M7-A8[2], M27-A3[3]). The compounds were tested in the range from 012-128 µg/ml. Colonies were taken directly from a second-pass culture plate and prepared to a suspension equivalent to the 0.5 McFarland standard using normal saline. Inoculation of the MIC plates took place within 15 minutes after adjustment of the inoculum suspension turbidity. The panels were incubated at 35° C. for 16 to 20 hours before reading the MIC endpoints. The compounds of Examples 4 to 8 were dissolved in DMSO to make the initial solutions of 5120 µg/ml. These solutions were diluted 1:10 in sterile water to a stock solution of 512 µg/ml. The stock solutions were further diluted into the appropriate broth medium for the sequential dilutions used in the broth microdilution panels. S. pneumoniae was tested in Mueller Hinton (MH) broth with 3% lysed horse blood and C. albicans was tested in RPMI-1640 medium. All other organisms were tested in MH broth.

The most active compound was found to be Example 7 which exhibited MICs of 0.06 µg/ml against both MRSA and MSSA strains.

3. In Vivo Antibacterial Activity of Example 1 (E1) Both Parenterally and Orally An experimental model of infection by S. aureus was used to assess the antibacterial activity of FabI inhibitors.

Briefly in vivo studies were performed using groups of 5 week-old neutropenic female Swiss mice (five mice per group for each condition).

The virulent methicillin susceptible Staphylococcus aureus strain ATCC 29213 was grown to exponential phase in Tryptic soy (TS) broth culture. The bacterial culture was diluted to obtain a bacterial suspension of 1-3 $10^9$ cfu/ml, washed in physiological serum and resuspended in mucin 10% contained physiological serum. The bacterial suspension was then inoculated to mice (200 µl per mouse) by intraperitoneal injection. The inoculums count was verified by plating 10-fold dilutions of the suspension on TS agar plates immediately after inoculation.

To test the hypothesis of a protection of the compound of E1 after parenteral administration, the test compound was dissolved and diluted in a formulation containing 20% hydroxy-propyl beta cyclodextrine (HPCD) and glucose 1% and an appropriate volume of the solution (corresponding to dose levels of 6.25 and 12.5 mg/kg of body weight) was administered subcutaneously to each mouse, just after the bacterial infection. The negative control group received the 20% HPCD solution alone and vancomycin at 6.25 mg/kg was used as the positive control.

To assess for protection after oral administration, the compound of E1 was dissolved and diluted in a formulation containing 1% dimethyl sulfoxide (DMSO) and 10% cremophor EL and an appropriate volume of the solution (corresponding to dose levels of 100 and 200 mg/kg of body weight) was administered orally to each mouse, just after the bacterial infection. The negative control group received the 1% DMSO and 10% cremophor EL solution alone.

Mice health and clinical signs were recorded during 48 h and results were reported as survival rate.

All animal experiments were carried out in accordance with institutional guidelines. Compound activity is measure by its effect at a given dose to reduce the bacterial burden in the thigh of infected mice.

Figure 2:
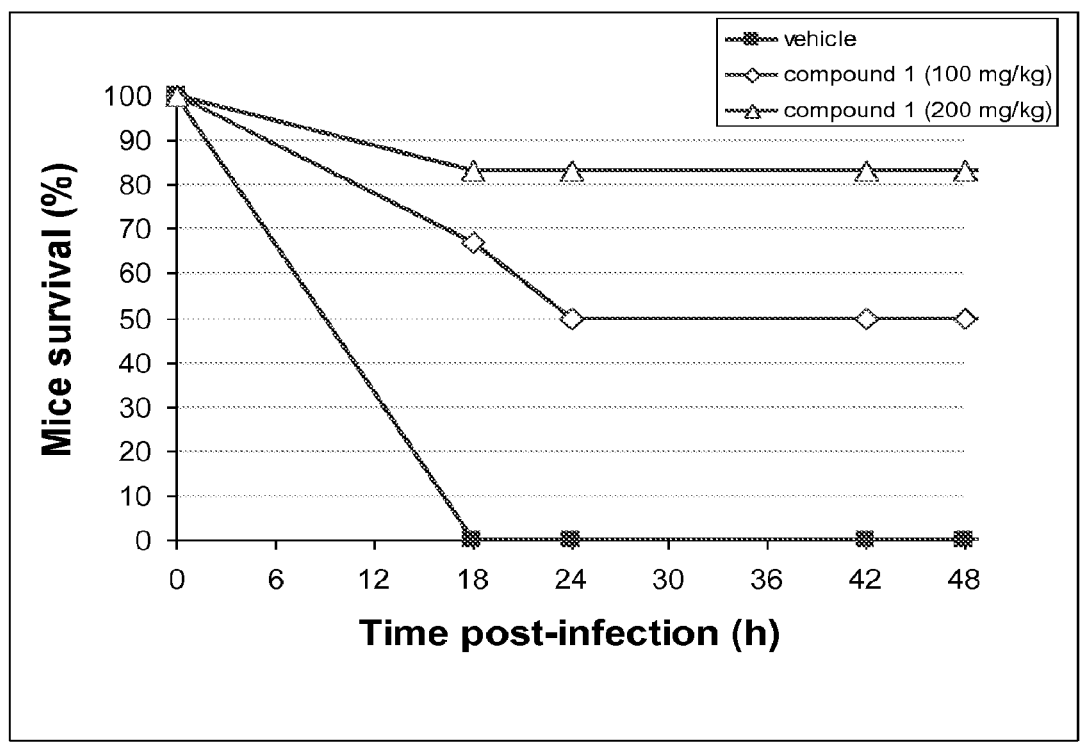
FIG. 2 relates to survival of infected mice after a single oral treatment of the compound of Example 1.

As shown in FIGS. 1 and 2, results of in vivo protection assay indicate that the compound of E1 (compound 1) is able to protect mice against bacterial dissemination after both parenteral and oral administration at dose levels of 6.25 and

TABLE 3

Representative Examples of MIC (µg/ml) (Broth microdilution) of compounds of Examples 4-8:

| Example | MRSA (IHMA #510059) | MSSA (IHMA #555189) | E. coli (ATCC 25922) | E. faecalis (ATCC 29212) | S. pneumoniae (ATCC 49619) | C. albicans (ATCC 90028) |
|---|---|---|---|---|---|---|
| 4 | 32 | 4 | — | — | — | — |
| 5 | 1 | 0.015 | — | — | — | — |
| 6 | 4 | 0.25 | — | — | — | — |
| 7 | 0.06 | 0.06 | 4 | 64 | >128 | >128 |
| 8 | 1 | 0.06 | — | — | — | — |

12.5 mg/kg (subcutaneous administration) and dose levels of 100 and 200 mg/kg (oral administration).

4. HSA Binding Analysis of Example 7 (E7) Using a Chiral HSA Column

Test System

The test system used in this analysis was an HSA chiral column.

Reagents and Chemicals

Potassium phosphate monobasic $KH_2PO_4$ and potassium phosphate dibasic trihydrate $K_2HPO_4$, $3H_2O$ were obtained from Calbiochem. Acetonitril, DMSO and sodium azide were purchased from Sigma-Aldrich. 2-propanol was provided by Fluka. Water was MilliQ grade obtained from Millipore system Milli-Q Plus (Waters).

Preparation of Reagents 20 mM $K_2HPO_4$: 4.564 g in 1 L of water 20 mM $KH_2PO_4$: 2.722 g in 1 L of water 20 mM Phosphate buffer pH 7.0: 58.7% of 20 mM $K_2HPO_4$ + 41.3% of 20 mM $KH_2PO_4$ (the pH is adjusted if necessary).

Preparation of Stock Solutions, Calibration and Quality Control Samples

A 10 mM stock solution of Example 7 (molecular weight of 475.49 and HPLC purity 86.3%) was prepared by dissolving 1.8 mg of a compound of Example 7 in 0.327 ml of DMSO. The compound of Example 7 at a concentration of 100 µM was prepared by diluting the stock solution at 10 mM in DMSO with Potassium phosphate buffer pH 7.0.

Equipment

HPLC system Alliance 2690 (Waters)

PDA UV detector 996 (Waters)

Column Chiral HSA 50×3.0 mm, 5 µm (Chromtec)

AT261 scale (Mettler-Toledo)

pH-meter easy seven (Mettler-Toledo)

Pipetman (Eppendorf)

Vortex (Fisher-Bioblock)

Ultrasound bath 4 mL glass vials (Dutscher)

2 mL glass vials for chromatography (Interchim)

Liquid Chromatography Parameters

Liquid Chromatography was used in accordance with the parameters shown in Table 4:

TABLE 4

| Chromatographic parameters | |
|---|---|
| HPLC system | Alliance 2690 (Waters) |
| Column | Chiral HSA 50 × 3.0 mm, 5 µm (Chromtec) |
| Flow rate | 0.5 mL/min |
| Column temperature | 37° C. |
| Auto sampler temperature | 10° C. |
| Mobile Phase | 94% 20 mM Potassium phosphate buffer pH 7.0 6% 2-propanol |
| Detection | Dual λ Absorbance Detector (UV spectrum) From 200 to 400 nm, extracting λ max |
| Injected volume | 10 µL |
| Monitoring and processing data softwares | Empower |

Percentage Binding Calculation

The relationship between the retention time (Tr) and percentage of protein binding (PB %) depended on the dead time (T0) and the capacity factor (k'):

$$PB\% = [k'/(k'+1)]*100$$

where k'=(Tr−T0)/T0

Results

The compound of Example 7 was found to demonstrate moderate binding to HSA as may be seen from the results shown in Table 5:

TABLE 5

HSA binding data for Example 7

| Test Number | λmax (nm) | T0 (min) | Tr (min) | k' | k' (average) | C (average) | HSA Binding (%) |
|---|---|---|---|---|---|---|---|
| 1 | 318 | 0.770 | 3.070 | 2.987 | 2.987 | 0.75 | 74.9 |
| 2 | | 0.772 | 3.073 | 2.981 | | | |
| 3 | | 0.769 | 3.071 | 2.993 | | | |

CLSI Guideline References

1. M100-S20

Clinical and Laboratory Standards Institute, 2010. *Performance Standards for Antimicrobial Susceptibility Testing; Twentieth Informational Supplement*. CLSI document M100-S20. Clinical and Laboratory Standards Institute (CLSI), Wayne, Pa. 19087-1898 USA.

2. M7-A8

Clinical and Laboratory Standards Institute (CLSI), 2009. *Methods for Dilution Antimicrobial Test for Bacteria That Grow Aerobically; Approved Standard-Eighth Edition*. CLSI document M07-A8 [ISBN 1-56238-689-1]. CLSI, 940 West Valley Road, Suite 1400, Wayne, Pa. 19087 USA.

3. M27-A3

Clinical and Laboratory Standards Institute, 2009. *Reference method for broth dilution antifungal broth susceptibility testing of yeasts-Approved Standard Third Edition*. CLSI document M27-A3. Clinical and Laboratory Standards Institute (CLSI), Wayne, Pa. 19087-1898 USA.

The invention embraces all combinations of preferred and more preferred groups and suitable and more suitable groups and embodiments of groups recited above.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims.

We claim:

1. A method of treatment of microbial infections which comprises administering to a patient in need thereof an efficient amount of a compound of formula (I):

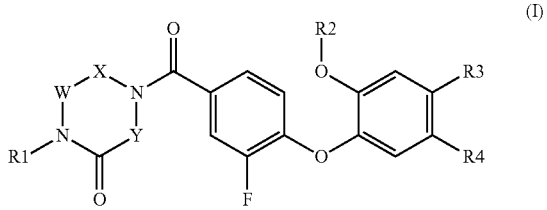

wherein:
- W, X and Y independently represent CH₂ or C=O, wherein said CH₂ group may be optionally independently substituted by a fluorine or (C₁-C₆) alkyl group, wherein said (C₁-C₆) alkyl group may be further substituted by one or two R5 groups;
- R1 represents H, (C₁-C₆) alkyl optionally substituted by a CONR$_a$R$_b$ group, (C₂-C₆) alkenyl, (C₂-C₆) alkynyl, phenyl or a —Z-Het group, such that Z represents a bond or a linker selected from CO, (C₁-C₆) alkylene or —CO—(C₁-C₆) alkylene and Het represents a 4-6 membered monocyclic saturated or unsaturated heterocycle containing 1-3 heteroatoms selected from N, O and S, wherein said phenyl or heterocycle group of R1 may be optionally substituted by one or more R5 groups;
- R2 represents H, CO₂R$_a$, COR$_a$, CONR$_a$R$_b$, CH₂OR$_c$, CH₂NR$_a$R$_b$, SO₂NR$_a$R$_b$ or P(O)OR$_a$OR$_b$;
- R3 represents halogen, (C₁-C₆) alkyl, (C₂-C₆) alkenyl or (C₂-C₆) alkynyl;
- R4 represents H, halogen, CN or CH₃;
- R$_a$, R$_b$ and R$_c$, independently represent H, (C₁-C₆) alkyl, (C₂-C₆) alkenyl, (C₂-C₆) alkynyl, or an NR$_a$R group may optionally form a 3- to 7-membered nitrogen containing saturated heterocycle optionally containing 1 to 3 additional heteroatoms selected from N, O or S wherein said heterocycle may be optionally substituted by one or more (C₁-C₆) alkyl groups;
- R5 represents halogen, CN, (C₁-C₆) alkyl, (C₂-C₆) alkenyl, (C₂-C₆) alkynyl, CO₂R$_a$, COR$_a$, CONR$_a$R$_b$ OCOR$_a$, OR$_a$, NR$_a$R$_b$, ON=CR$_a$R$_b$, NR$_c$COR$_a$, NR$_c$COOR$_a$, OCONR$_a$R$_b$, NR$_c$CONR$_a$R$_b$, NR$_c$SO₂R$_a$, S(O)$_n$R$_a$, or SO₂NR$_a$R$_b$;
- n represents an integer selected from 0 to 2;

or a pharmaceutically acceptable salt or solvate thereof.

2. A method as defined in claim 1 wherein said microbial infection is a human or animal infection by microbial pathogens selected from the group consisting of *Staphylococcus aureus, Acinetobacter baumannii, Bacillus anthracis, Chlamydophila pneumoniae, Escherichia coli, Haemophilus influenzae, Helicobacter pylori, Klebsiella pneumoniae, Neisseria meningitidis, S. intermedius, P. multocida, B. bronchiseptica, M. haemolytica, A. pleuropneumoniae, Mycobacterium tuberculosis* and *Plasmodium falciparum*.

3. A method as defined in claim 2 wherein said microbial infection is a human or animal infection by *Staphylococcus aureus*.

4. A method as defined in claim 3 wherein said microbial infection is a human or animal infection by a strain of *Staphylococcus aureus* selected from the group consisting of methicillin-susceptible *Staphylococcus aureus* (MSSA), methicillin-resistant *Staphylococcus aureus* (MRSA), vancomycin-intermediate *Staphylococcus aureus* (VISA) and vancomycin-resistant *Staphylococcus aureus* (VRSA).

5. The method of claim 1, wherein W, X and Y each represent CH₂ optionally independently substituted by an unsubstituted (C₁-C₆) alkyl group.

6. The method of claim 1, wherein W represents C=O and X and Y both represent CH₂.

7. The method of claim 1, wherein W, X and Y each represent CH₂.

8. The method of claim 1, wherein R1 represents H, (C₁-C₆) alkyl, (C₂-C₆) alkenyl or (C₂-C₆) alkynyl.

9. The method of claim 1, wherein R1 represents H, (C₁-C₆) alkyl, (C₁-C₆) alkyl optionally substituted by a CONRaRb group or a —Z-Het group.

10. The method of claim 1, wherein R2 represents H, CO₂R$_a$, COR$_a$, CONR$_a$R$_b$, CH₂OR$_c$, or CH₂NR$_a$R$_b$.

11. The method of claim 1, wherein R3 represents halogen or (C₁-C₆) alkyl.

12. The method of claim 1, wherein R$_c$ represents H or (C₁-C₆) alkyl.

13. The method of claim 1 wherein the compound of formula (I) is:
- 4-[4-(4-Ethyl-5-fluoro-2-hydroxyphenoxy)-3-fluorobenzoyl]piperazin-2-one (EI);
- 4-[4-(4-Ethyl-2-hydroxyphenoxy)-3-fluorobenzoyl]piperazin-2-one (E2);
- 4-Fluoro-2-{2-fluoro-4-[(3-oxopiperazin-1-yl)carbonyl]phenoxy}-5-ethylphenyl ethyl carbonate (E3);
- 4-[4-(4-Ethyl-5-fluoro-2-hydroxyphenoxy)-3-fluorobenzoyl]piperazine-2,6-dione (E4);
- 4-[4-(4-Ethyl-5-fluoro-2-hydroxyphenoxy)-3-fluorobenzoyl]-1-methylpiperazin-2-one (E5);
- 2-[4-(4-(4-Ethyl-5-fluoro-2-hydroxyphenoxy)-3-fluorobenzoyl]-2-oxopiperazin-1-yl)acetamide (E6);
- 4-[4-(4-Ethyl-5-fluoro-2-hydroxyphenoxy)-3-fluorobenzoyl]-1-(morpholinomethyl)piperazin-2-one (E7); or
- 4-[4-(4-Ethyl-5-fluoro-2-hydroxyphenoxy)-3-fluorobenzoyl]-3-methyl piperazin-2-one (E8);

or a pharmaceutically acceptable salt or solvate thereof.

14. The method of claim 1 wherein the compound of formula (I) is 4-[4-(4-Ethyl-5-fluoro-2-hydroxyphenoxy)-3-fluorobenzoyl]-1-(morpholinomethyl)piperazin-2-one (E7).

15. The method of claim 8 wherein R1 represents H or (C₁-C₆) alkyl.

16. The method of claim 9, wherein R1 represents —CH—CONH₂ or —CH₂—morpholinyl.

17. The method of claim 10, wherein R2 represents H or —CO₂-ethyl.

18. The method of claim 11, wherein R3 represents ethyl.

19. The method of claim 1, wherein R4 represents H or F.

20. The method of claim 1, wherein R$_a$ and R$_b$ represent H.